US010165968B2

United States Patent
Choi et al.

(10) Patent No.: US 10,165,968 B2
(45) Date of Patent: Jan. 1, 2019

(54) BLOOD GLUCOSE MEASUREMENT APPARATUS AND BLOOD GLUCOSE MEASUREMENT METHOD THEREOF

(71) Applicant: Samsung Electronics Co., Ltd., Gyeonggi-do (KR)

(72) Inventors: Hyoung-seon Choi, Seoul (KR); Chul-ho Cho, Gyeonggi-do (KR); Seong-je Cho, Gyeonggi-do (KR); Kwang-bok Kim, Incheon (KR); Seung-min Lee, Seoul (KR); Sun-tae Jung, Gyeonggi-do (KR); Jae-geol Cho, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 157 days.

(21) Appl. No.: 15/148,537

(22) Filed: May 6, 2016

(65) Prior Publication Data

US 2016/0331285 A1 Nov. 17, 2016

Related U.S. Application Data

(60) Provisional application No. 62/160,351, filed on May 12, 2015.

(30) Foreign Application Priority Data

Aug. 20, 2015 (KR) .................. 10-2015-0117340

(51) Int. Cl.
*A61B 5/145* (2006.01)
*A61B 5/11* (2006.01)
(Continued)

(52) U.S. Cl.
CPC ...... *A61B 5/14532* (2013.01); *A61B 5/02055* (2013.01); *A61B 5/02438* (2013.01);
(Continued)

(58) Field of Classification Search
CPC ............ A61B 5/14532; A61B 5/02055; A61B 5/02438; A61B 5/11; A61B 5/14514;
(Continued)

(56) References Cited

U.S. PATENT DOCUMENTS 8,517,941 B1    8/2013  Wenzel
9,750,877 B2 *  9/2017  Kovelman .......... A61M 5/1723
(Continued)

FOREIGN PATENT DOCUMENTS

EP    2 762 076    8/2014
EP    2 901 926    8/2015
(Continued)

OTHER PUBLICATIONS

International Search Report dated Jun. 24, 2016 issued in counterpart application No. PCT/KR2016/003298, 12 pages.
(Continued)

*Primary Examiner* — Navin Natnithithadha
(74) *Attorney, Agent, or Firm* — The Farrell Law Firm, P.C.

(57) ABSTRACT

Methods and apparatuses for blood glucose measurement are provided. A first glucose concentration in a body fluid of a user is detected based on a first measurement interval. A first blood glucose level of the user is determined based on the first glucose concentration. A glucose concentration measurement interval is changed from the first measurement interval to a second measurement interval according to an occurrence of an event. A second glucose concentration in the body fluid is detected based on the second measurement interval. A second blood glucose level of the user is determined based on the second glucose concentration.

20 Claims, 19 Drawing Sheets

(51) Int. Cl.
*G06F 19/00* (2018.01)
*A61B 5/00* (2006.01)
*A61B 5/0205* (2006.01)
*A61B 5/024* (2006.01)

(52) U.S. Cl.
CPC .......... *A61B 5/11* (2013.01); *A61B 5/14514* (2013.01); *A61B 5/14517* (2013.01); *A61B 5/14546* (2013.01); *A61B 5/4809* (2013.01); *A61B 5/681* (2013.01); *A61B 5/6833* (2013.01); *A61B 5/7275* (2013.01); *A61B 5/7282* (2013.01); *A61B 5/749* (2013.01); *A61B 5/7435* (2013.01); *A61B 5/7465* (2013.01); *G06F 19/00* (2013.01); *A61B 2503/10* (2013.01); *A61B 2562/0219* (2013.01); *A61B 2562/0223* (2013.01)

(58) Field of Classification Search
CPC .......... A61B 5/14517; A61B 5/14546; A61B 5/4809; A61B 5/681; A61B 5/6833; A61B 5/7275; A61B 5/7282; A61B 5/7435; A61B 5/7465; A61B 5/749; A61B 2503/10; A61B 2562/0219; A61B 2562/0223
USPC .......................................... 600/309, 345–366
See application file for complete search history.

(56) References Cited

U.S. PATENT DOCUMENTS

| 9,750,878 B2* | 9/2017 | Roy ................... A61M 5/1723 |
| 2003/0125612 A1* | 7/2003 | Fox ................... A61B 5/14532 |
| | | 600/347 |
| 2009/0054753 A1 | 2/2009 | Robinson et al. |
| 2012/0215085 A1 | 8/2012 | Werner et al. |
| 2013/0109943 A1 | 5/2013 | Gottlieb et al. |

FOREIGN PATENT DOCUMENTS

| KR | 1020090037482 | 4/2009 |
| KR | 1020120113530 | 10/2012 |
| WO | WO 2012/170586 | 12/2012 |
| WO | WO 2013/146242 | 10/2013 |
| WO | WO 2013/163342 | 10/2013 |

OTHER PUBLICATIONS

European Search Report dated Feb. 23, 2018 issued in counterpart application No. 16792846.4-1115, 11 pages.

* cited by examiner

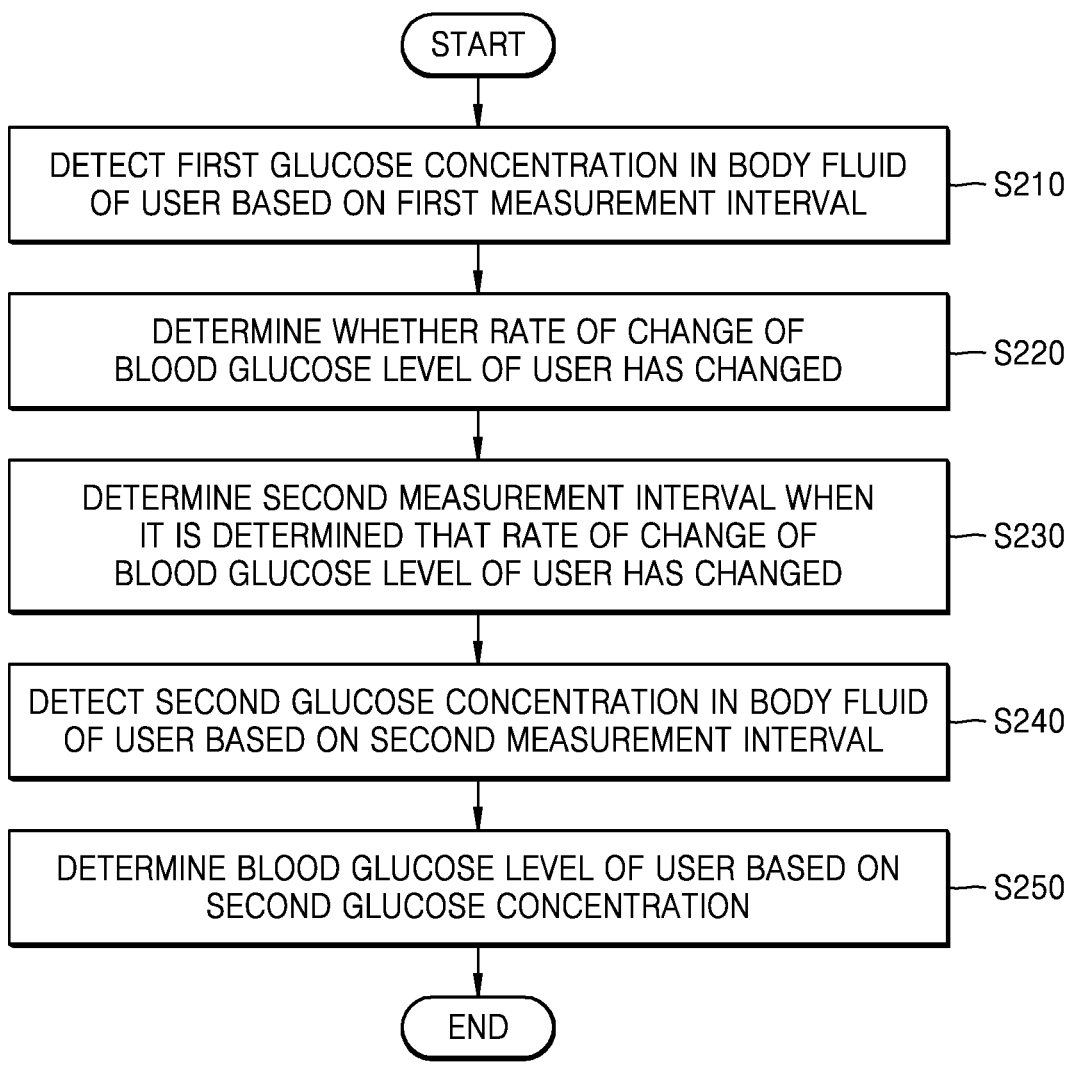

BLOOD GLUCOSE MEASUREMENT APPARATUS AND BLOOD GLUCOSE MEASUREMENT METHOD THEREOF

PRIORITY

This application claims priority under 35 U.S.C. § 119(e) to U.S. Provisional Application No. 62/160,351, filed in the U.S. Patent and Trademark Office on May 12, 2015, and under 35 U.S.C. § 119(a) to Korean Patent Application No. 10-2015-0117340, filed in the Korean Intellectual Property Office of Aug. 20, 2015, the disclosures of which are incorporated herein by reference.

BACKGROUND

1. Field of the Disclosure

The present disclosure relates generally to an apparatus for measuring a blood glucose level of a user and a method thereof, and more particularly, to measurement of a blood glucose level of a user based on intervals before and after an event.

2. Description of the Related Art

The blood glucose level of user may be measured by collecting blood and measuring a glucose concentration in the collected blood. However, sticking the skin to collect the blood of the user may be painful for the user.

Methods for measuring the blood glucose level of a user without collecting blood have been developed and include, for example, an electrochemical method of measuring a glucose concentration in a body fluid secreted inside of outside the skin, an optical method of measuring a glucose concentration by using the optical property of glucose inside a body, an exhalation measurement method of measuring glucose concentration by using a biomarker gas concentration in exhalation.

In the electrochemical method, the glucose concentration in blood is determined based on the glucose concentration in a body fluid. However, when the glucose concentration in blood, i.e., a blood glucose level, sharply changes, the glucose concentration in the body fluid may not reflect the glucose concentration in blood.

The sharp change in the blood glucose level may cause low or high blood glucose and several dangerous symptoms may occur. Thus, a user must be informed of a danger before low or high blood glucose occurs.

In addition, in the electrochemical method, a blood glucose measurement apparatus may be implemented by periodically measuring the glucose concentration in the body fluid while being attached to the skin of a user.

SUMMARY

The present disclosure has been made to address at least the above problems and/or disadvantages and to provide at least the advantages described below. Accordingly, an aspect of the present disclosure provides a method and an apparatus for accurately determining a blood glucose level of a user and reducing power consumption of a blood glucose measurement apparatus.

According to an aspect of the present disclosure, a blood glucose measurement apparatus is provided that includes a glucose detection unit configured to detect a glucose concentration in a body fluid of a user based on a glucose concentration measurement interval. The blood glucose measurement apparatus also includes a control unit configured to determine a first blood glucose level of the user based on a first glucose concentration detected at a first measurement interval, change the glucose concentration measurement interval from the first measurement interval to a second measurement interval according to an occurrence of an event, and determine a second blood glucose level of the user based on a second glucose concentration detected at a second measurement interval.

The blood glucose measurement apparatus may further include a communication unit configured to receive information about whether the event has occurred from a periphery device through short-distance wireless communication.

The event may include exercise performed by the user, and the control unit may be further configured to change the glucose concentration measurement interval from the first measurement interval to the second measurement interval based on the exercise performed by the user.

The control unit may be further configured to determine an amount of exercise performed by the user from a movement sensor attached to the user and change the glucose concentration measurement interval from the first measurement interval to the second measurement interval when the amount of exercise performed by the user exceeds a preset amount of exercise.

The event may include food consumption by the user, and the control unit may be further configured to change the glucose concentration measurement interval from the first measurement interval to the second measurement interval based on the food consumption by the user.

The event may include a determination that the user is in a sleeping state, and the control unit may be further configured to change the glucose concentration measurement interval from the first measurement interval to the second measurement interval based on the determination that the user is in the sleeping state.

The event may include a determination that an amount of hormones of the user has changed, and the control unit may be further configured to change the glucose concentration measurement interval from the first measurement interval to the second measurement interval based on the determination that an amount of hormones of the user has changed.

The control unit may be further configured to determine the second measurement interval as less than the first measurement interval according to an increase in a rate of change of the first blood glucose level of the user.

The control unit may be further configured to determine whether a rate of change of the first blood glucose level of the user exceeds a threshold value, and determine that the event has occurred when the rate of change of the first blood glucose level of the user exceeds the threshold value.

The control unit may be further configured to determine a rate of change of the first glucose concentration over time, and determine that the event has occurred according to a change in the rate of change of the first glucose concentration.

According to another aspect of the present disclosure, a blood glucose measurement method is provided. A blood glucose measurement apparatus detects a first glucose concentration in a body fluid of a user based on a first measurement interval. A first blood glucose level of the user is determined based on the first glucose concentration. A glucose concentration measurement interval is changed from the first measurement interval to a second measurement interval according to an occurrence of an event. A second glucose concentration in the body fluid is detected based on the second measurement interval. A second blood glucose level of the user is determined based on the second glucose concentration.

Information about whether the event has occurred may be received from a periphery device through short-range wireless communication.

The event may include exercise performed by the user, and the glucose concentration measurement interval is changed from the first measurement interval to the second measurement interval based on the exercise performed by the user.

The changing the glucose concentration measurement interval may include determining an amount of exercise performed by the user from a movement sensor attached to the user, and changing the glucose concentration measurement interval from the first measurement interval to the second measurement interval when the amount of exercise performed by the user exceeds a preset amount of exercise.

The event may include food consumption by the user, and the glucose concentration measurement interval is changed from the first measurement interval to the second measurement interval based on the food consumption by the user.

The event may include whether the user is in a sleeping state, and the glucose concentration measurement interval is changed from the first measurement interval to the second measurement interval based on the determination that the user is in the sleeping state.

The event may include a determination that an amount of hormones of the user has changed, and the glucose concentration measurement interval is changed from the first measurement interval to the second measurement interval based on the determination that an amount of hormones of the user has changed.

The changing the glucose concentration measurement interval may include determining the second measurement interval as less than the first measurement interval according to an increase in a rate of change of the first blood glucose level of the user.

The changing the glucose concentration measurement interval may include: determining whether a rate of change of the first blood glucose level of the user exceeds a threshold value and determining that the event has occurred when the rate of change of the first blood glucose level exceeds the threshold value.

The changing the glucose concentration measurement may include: determining a rate of change of the first glucose concentration over time, and determining that the event has occurred according to a change in the determined rate of change of first glucose concentration.

According to another aspect of the present disclosure, a computer recording medium recorded with a computer-readable instruction is provided. The instruction, which is executed by at least one processor, causes the processor to perform a method. The method includes detecting, by a blood glucose measurement apparatus, a first glucose concentration in a body fluid of a user based on a first measurement interval; determining a first blood glucose level of the user based on the first glucose concentration; changing a glucose concentration measurement interval from the first measurement interval to a second measurement interval according to an occurrence of an event; detecting a second glucose concentration in the body fluid based on the second measurement interval; and determining a second blood glucose level of the user based on the second glucose concentration.

BRIEF DESCRIPTION OF THE DRAWINGS

The above and other aspects, features, and advantages of the present disclosure will become more apparent from the following detailed description when taken in conjunction with the accompanying drawings, in which:

FIG. 2A is a flowchart illustrating a method by which a blood glucose measurement apparatus changes a glucose concentration measurement interval according to a rate of change of a blood glucose level of a user, according to an embodiment of the present disclosure;

DETAILED DESCRIPTION

Figure 1:
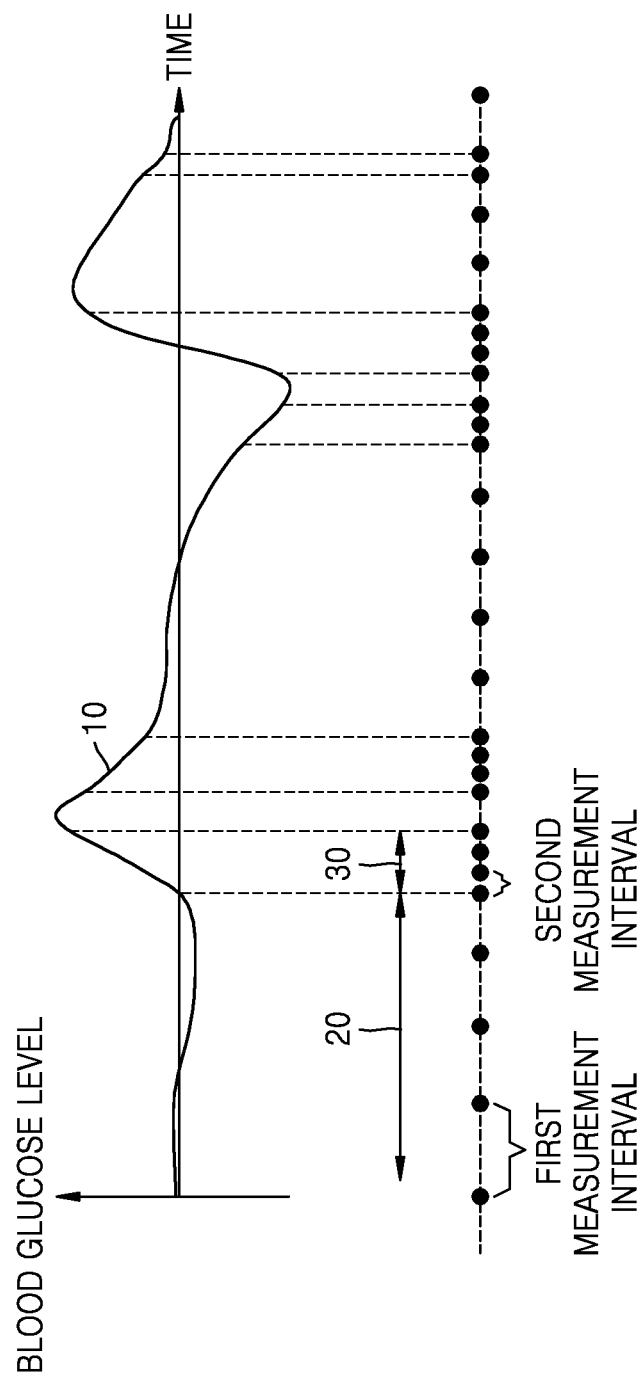
FIG. 1 is a graph showing a method by which a blood glucose measurement apparatus changes a glucose concentration measurement interval according to a rate of change of a blood glucose level of a user, according to an embodiment of the present disclosure.

Embodiments of the present disclosure are described in detail with reference to the accompanying drawings. The same or similar components may be designated by the same or similar reference numerals although they are illustrated in different drawings.

The terms used herein are general terms currently widely used in the art, but may vary according to the intention of those of ordinary skill in the art, precedents, or new technology in the art. Also, specified terms may be selected, and in this case, the detailed meanings thereof will be described herein. Thus, the terms used herein should be understood not as simple names but as based on the meanings of the terms and the overall description.

It will also be understood that when a component "includes" an element, unless there is an opposing description, the component does not exclude, and may further include another element. In addition, terms such as "unit", "module", and the like refer to units that perform at least one function or operation, and units may be implemented as hardware, software, or a combination of hardware and software.

As used herein, the phrase "blood glucose level of a (the) user" may indicate a glucose concentration in blood of the user.

As used herein, the term "event" may be when a rate of change of a blood glucose level of the user exceeds a threshold value. In addition, as used herein, the term "event" may refer to a motion of the user or a body condition of the user, which changes the rate of change of the blood glucose level of the user. For example, the event may be exercise, food intake, sleeping, or a change in hormones of the user, but is not limited thereto.

As used herein, the term "and/or" includes any and all combinations of one or more of the associated listed items. Expressions such as "at least one of," when preceding a list of elements, modify the entire list of elements and do not modify the individual elements of the list.

FIG. 1 is a graph for illustrating a method by which a blood glucose measurement apparatus changes a glucose concentration measurement interval according to a rate of change of a blood glucose level of a user, according to an embodiment of the present disclosure.

The blood glucose level of the user may indicate a glucose concentration in the blood of the user and may be measured based on the blood of the user, which has been collected through blood-collection.

The blood glucose level of the user may be directly measured from the blood of the user through blood-collection or may be determined based on a glucose concentration measured from an interstitial fluid or sweat, since glucose in blood spreads to an interstitial fluid in the skin. This method is referred to as an electrochemical method.

The blood glucose measurement apparatus 100 measures a glucose concentration in a body fluid of the user, which is spread from the blood, and determines the blood glucose level of the user based on the measured glucose concentration. The body fluid of the user may include an interstitial fluid, sweat, tears, or saliva, but is not limited thereto.

It takes a certain amount of time for glucose in blood to fully spread to an interstitial fluid. Therefore, as a rate of change of glucose concentration in the blood increases, a difference between the glucose concentration in the blood and the glucose concentration in the interstitial fluid increases.

Accordingly, the blood glucose measurement apparatus 100 determines a more accurate blood glucose level of the user by more frequently measuring glucose concentration as the rate of change of the blood glucose level of the user increases.

A blood glucose level graph 10 of FIG. 1 shows a change in the blood glucose level of the user over time.

In the blood glucose level graph 10, a first duration 20 is a duration in which the blood glucose level is not changed significantly, and a second duration 30 is a duration in which the blood glucose level is sharply changed. The blood glucose measurement apparatus 100 measures the glucose concentration at a first measurement interval during the first duration 20, and measures the glucose concentration at a second measurement interval, which is shorter than the first measurement interval, during the second duration 30.

Accordingly, the blood glucose measurement apparatus 100 determines a more accurate blood glucose level of the user and reduce an amount of power consumed to measure the glucose concentration.

FIG. 2A is a flowchart illustrating a method by which the blood glucose measurement apparatus changes a glucose concentration measurement interval according to a rate of change of a blood glucose level of a user, according to an embodiment of the present disclosure.

In step S210, the blood glucose measurement apparatus 100 detects a first glucose concentration in a body fluid of the user based on a first measurement interval.

The blood glucose measurement apparatus 100 may be attached to the skin of the user. For example, the blood glucose measurement apparatus 100 may be embodied as a patch attached to the skin, a lens attached to the eye, or a watch attached to the wrist.

Additionally, the blood glucose measurement apparatus 100 may include a glucose oxidizing enzyme for oxidizing glucose. The blood glucose measurement apparatus 100 may oxidize glucose that is spread and secreted from the blood with the glucose oxidizing enzyme, electrolyze an oxidized and formed substance, and then measure the first glucose concentration based on a current generated by means of the electrolysis.

For example, hydrogen peroxide ($H_2O_2$) may be generated by oxidizing glucose with the glucose-oxidizing enzyme. Accordingly, one molecule of $H_2O_2$ may give two electrons at an electrode in the blood glucose measurement apparatus 100, thereby generating two electrons per glucose molecule. Therefore, the blood glucose measurement apparatus 100 may determine the first glucose concentration based on a measured amount of current.

The blood glucose measurement apparatus 100 may determine the blood glucose level of the user based on the first glucose concentration. The blood glucose measurement apparatus 100 may determine the first glucose concentration as the blood glucose level of the user, or may determine the blood glucose level of the user by correcting the first glucose concentration based on a pattern of a difference between the glucose concentration in the body fluid and the glucose concentration in the blood.

The blood glucose measurement apparatus 100 may measure glucose concentration in sweat, tears, or saliva secreted outside the skin, and may measure glucose concentration in an interstitial fluid in the skin. When the glucose concentration in the interstitial fluid in the skin is measured, the blood glucose measurement apparatus 100 may include a microneedle. The microneedle may be injected into the skin of the user when the blood glucose measurement apparatus 100 is attached to the user.

In step S220, the blood glucose measurement apparatus 100 determines whether the rate of change of the blood glucose level of the user has changed.

The blood glucose measurement apparatus 100 may determine a rate of change of the first glucose concentration over time, and determine the rate of change of the blood glucose level of the user based on the rate of change of the first glucose concentration. The blood glucose measurement apparatus 100 may determine the rate of change of the first glucose concentration as the rate of change of the blood glucose level of the user, or may determine a value, which is corrected from the rate of change of the first glucose concentration, as the rate of change of the blood glucose level of the user. Accordingly, the blood glucose measurement apparatus 100 may determine that the rate of change of the blood glucose level of the user has changed, when it is determined that the rate of change of the first glucose concentration has changed.

Alternatively, the blood glucose measurement apparatus 100 may receive motion information of the user from a movement sensor attached to the user, and may determine, based on the motion information, whether the rate of change of the blood glucose level of the user has changed.

Alternatively, the blood glucose measurement apparatus 100 may determine an amount of exercise performed by the user based on the motion information of the user, and may determine that the rate of change of the blood glucose level of the user has changed when the determined amount of exercise performed by the user exceeds a preset amount of exercise.

Alternatively, the blood glucose measurement apparatus 100 may determine that the rate of change of the blood glucose level of the user has changed when the user consumes food.

Alternatively, the blood glucose measurement apparatus 100 may determine that the rate of change of the blood glucose level of the user has changed when the user is in a sleeping state.

Alternatively, the blood glucose measurement apparatus 100 may determine that the rate of change of the blood glucose level of the user has changed when an amount of hormones of the user changes.

According to an embodiment of the present disclosure, the blood glucose measurement apparatus 100 may determine the rate of change of the blood glucose level of the user based on an amount of exercise performed by the user. Alternatively, the blood glucose measurement apparatus 100 may determine the rate of change of the blood glucose level of the user based on information about food consumed by the user. The information about the food consumed by the user may include information about a time taken to consume the food and types and calories of the consumed food, but is not limited thereto. Alternatively, the blood glucose measurement apparatus 100 may determine the rate of change of the blood glucose level of the user based on whether the user is in a sleeping state. Alternatively, the blood glucose measurement apparatus 100 may determine the rate of change of the blood glucose level of the user based on a change in hormones of the user. When the rate of change of the blood glucose level of the user is determined, the blood glucose measurement apparatus 100 may determine whether the rate of change of the blood glucose level of the user has changed.

In step S230, the blood glucose measurement apparatus 100 determines the second measurement interval, when it is determined that the rate of change of the blood glucose level of the user has changed.

The blood glucose measurement apparatus 100 may decrease a measurement interval, when the rate of change of the blood glucose level of the user increases. For example, when the rate of change of the blood glucose level of the user increases, the blood glucose measurement apparatus 100 may determine a value less than the first measurement interval as the second measurement interval. Alternatively when the rate of change of the blood glucose level of the user exceeds a threshold value, the blood glucose measurement apparatus 100 may determine a value less than the first measurement interval as the second measurement interval. The threshold value may be, for example, 1.5 mg/dL/min through 3 mg/dL/min.

In step S240, the blood glucose measurement apparatus 100 detects the second glucose concentration in the body fluid based on the determined second measurement interval.

In step S250, the blood glucose measurement apparatus 100 determines the blood glucose level of the user based on the second glucose concentration.

Figure 2B:
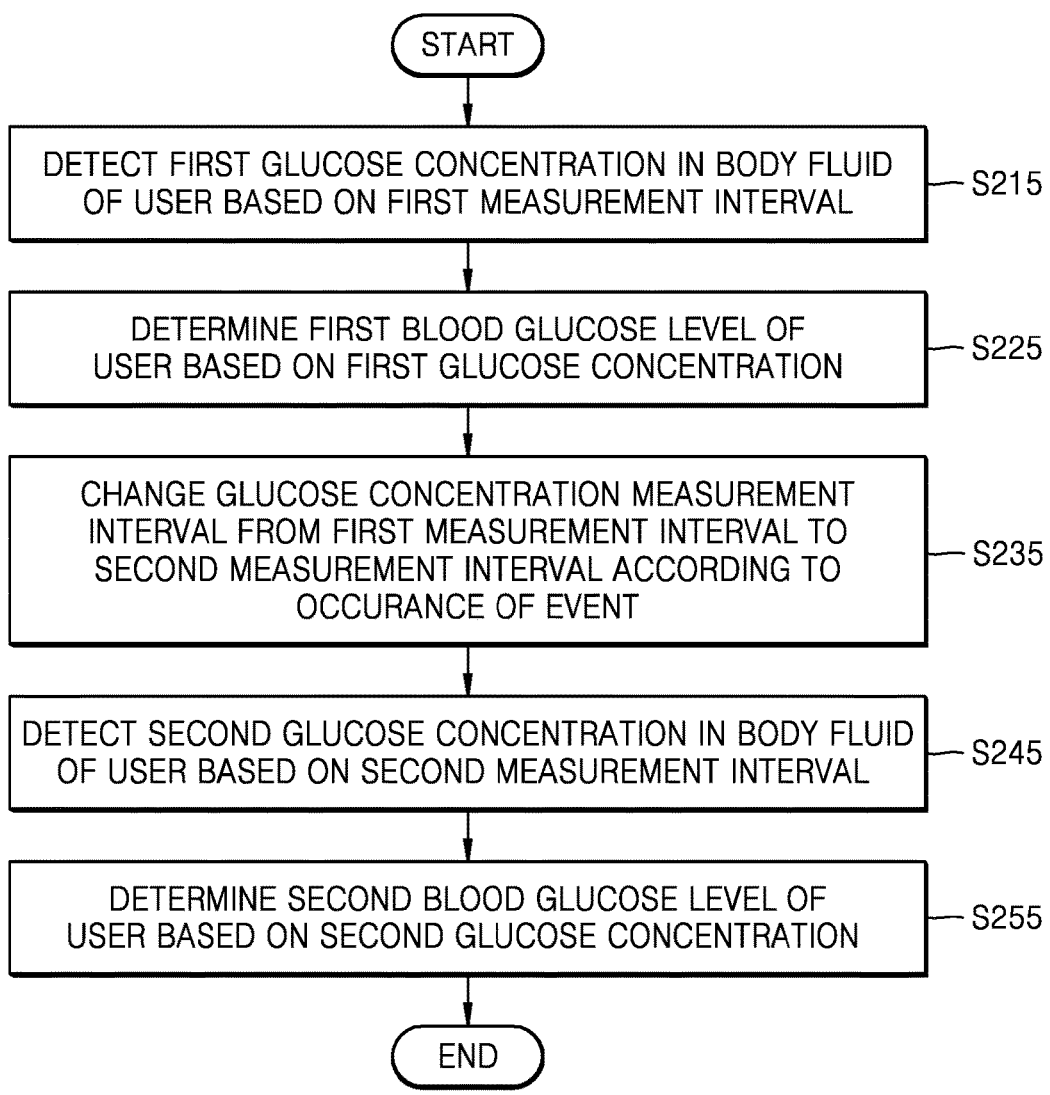
FIG. 2B is a flowchart illustrating a method by which a blood glucose measurement apparatus changes a glucose concentration measurement interval according to the occurrence of an event, according to an embodiment of the present disclosure.

FIG. 2B is a flowchart illustrating a method by which the blood glucose measurement apparatus changes a glucose concentration measurement interval according to the occurrence of an event, according to an embodiment of the present disclosure.

In step S215, the blood glucose measurement apparatus 100 detects a first glucose concentration in a body fluid of a user based on the first measurement interval. A detailed description of step S215 is provided above with respect to step S210 of FIG. 2A.

In step S225, the blood glucose measurement apparatus 100 determines a first blood glucose level of the user based on the first glucose concentration.

In step S235, the blood glucose measurement apparatus 100 changes the glucose concentration measurement interval from the first measurement interval to the second measurement interval according to the occurrence of an event.

An event may include, for example, when a rate of change of the blood glucose level of the user exceeds a threshold value. In addition, an event may be a motion of the user or a body condition of the user, which changes the rate of change of the blood glucose level of the user. For example, the event may be exercise, food intake, sleeping, or a change in hormones of the user, but is not limited thereto.

For example, when it is detected that the user has started or stopped exercising, the blood glucose measurement apparatus 100 may determine that an event has occurred. Alternatively, when it is detected that the user has started or ended food intake, the blood glucose measurement apparatus 100 may determine that an event has occurred. Alternatively, when it is detected that the user has been entered into or has awakened from a sleeping state, the blood glucose measurement apparatus 100 may determine that an event has occurred. Alternatively, when it is detected that an amount of hormones of the user has changed, the blood glucose measurement apparatus 100 may determine that an event has occurred.

Alternatively, when an amount of exercise performed by the user exceeds a predefined amount, or when a time taken to consume food exceeds a predefined time, the blood glucose measurement apparatus 100 may determine that an event has occurred.

Types of events, or a method of determining that an event has occurred, may be predefined in the blood glucose measurement apparatus 100 or may be set by the user.

When it is determined that an event has occurred, the blood glucose measurement apparatus 100 may change the glucose concentration measurement interval from the first measurement interval to the second measurement interval.

In addition, when it is determined that an event has occurred, the blood glucose measurement apparatus 100 may determine that the rate of change of the blood glucose level of the user has changed.

In step S245, the blood glucose measurement apparatus 100 detects a second glucose concentration in the body fluid based on the second measurement interval. In step S255, the blood glucose measurement apparatus 100 determines a second blood glucose level of the user based on the second glucose concentration. Steps S245 and S255 are described in greater detail above with respect to steps S240 and S250 of FIG. 2A.

Figure 3:
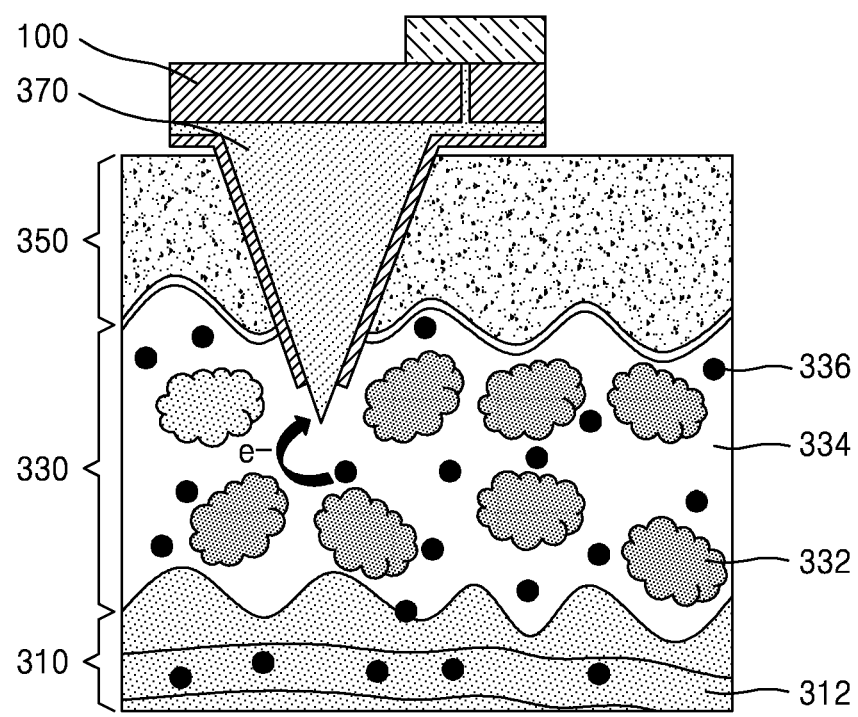
FIG. 3 is a diagram illustrating a method by which a blood glucose measurement apparatus measures a glucose concentration in an interstitial fluid, according to an embodiment of the present disclosure.

FIG. 3 is a diagram illustrating a method by which the blood glucose measurement apparatus measures glucose concentration in an interstitial fluid, according to an embodiment of the present disclosure.

Referring to FIG. 3, a blood glucose measurement apparatus 100 detects the glucose concentration in interstitial fluid 334 by using a microneedle 370.

Glucose 336 may move from a blood vessel 312 of a true skin layer 310 to the interstitial fluid 334 of an epidermal layer 330 according to a spreading phenomenon. Accordingly, the epidermal layer 330 includes cells 332, the interstitial fluid 334, and the glucose 336.

The blood glucose measurement apparatus 100 includes the microneedle 370, and the microneedle 370 is injected into the epidermal layer 330 by penetrating through a horny layer 350 of a user when the blood glucose measurement apparatus 100 is attached to the user.

When a glucose oxidizing enzyme is introduced to the interstitial fluid 334 through the microneedle 370, glucose molecules in the interstitial fluid 334 are oxidized so as to compose $H_2O_2$, the composed $H_2O_2$ is electrolyzed through the microneedle 370 such that electrons are given to the microneedle 370, and thus, a current flows through the microneedle 370. The blood glucose measurement apparatus 100 determines the glucose concentration in the interstitial fluid 334 in proportional to a magnitude of the current flowing through the microneedle 370.

Figure 4:
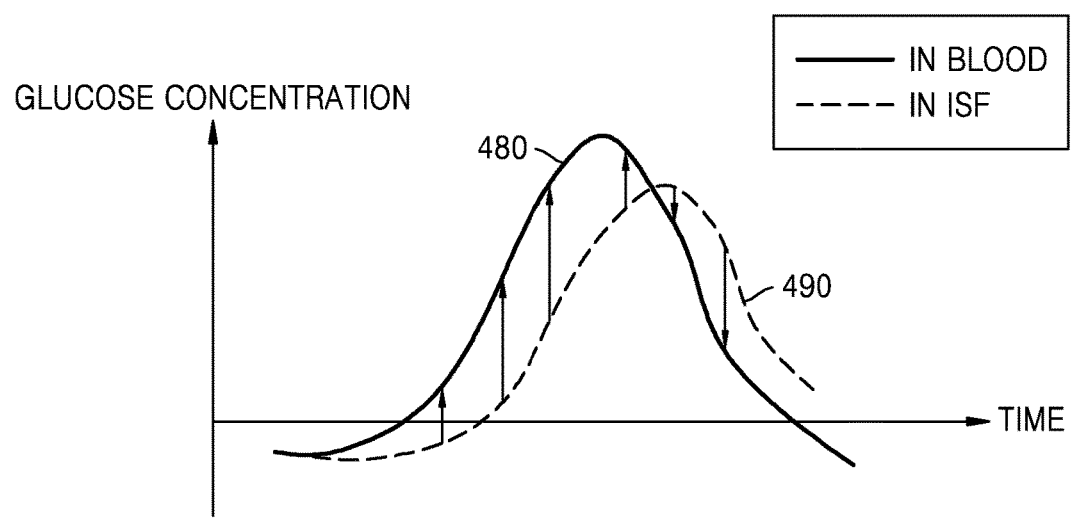
FIG. 4 is a graph showing a method by which a blood glucose measurement apparatus determines a blood glucose level of a user based on measured glucose concentration, according to an embodiment of the present disclosure.

FIG. 4 is a graph showing a method by which the blood glucose measurement apparatus determines a blood glucose level of the user based on the measured glucose concentration, according to an embodiment of the present disclosure.

Referring to FIG. 4, glucose concentration 480 in the blood vessel 312 may temporarily differ from glucose concentration 490 in the interstitial fluid 334.

For example, when the glucose concentration 480 in the blood vessel 312 quickly increases, it may take a certain amount of time for the glucose in the blood vessel 312 to fully spread into the interstitial fluid 334. Thus, the glucose concentration 490 in the interstitial fluid 334 may be lower than the glucose concentration 480 in the blood vessel 312 in the time it takes for the glucose in the blood vessel 312 to fully spread into the interstitial fluid 334. In this case, as a rate of change of the glucose concentration 480 in the blood vessel 312 increases, a difference between the glucose concentration 480 in the blood vessel 312 and the glucose concentration 490 in the interstitial fluid 334 increases.

Accordingly, as shown in FIG. 4, the blood glucose measurement apparatus 100 may determine a correction value based on a rate of change of the blood glucose level of the user, and may determine the blood glucose level of the user by adding the correction value to a measured value of the glucose concentration 490 in the interstitial fluid 334. For example, the blood glucose measurement apparatus 100 may determine the blood glucose level of the user by adding a larger correction value to the measured value of the glucose concentration 490 in the interstitial fluid 334 when a rate of increase of the blood glucose level of the user is larger. The blood glucose measurement apparatus 100 may store correction values with respect to rates of change of a blood glucose level.

In another example, when the glucose concentration 480 in the blood vessel 312 quickly decreases, it may take a long time for the glucose concentration 490 in the interstitial fluid 334 to be balanced with the glucose concentration 480 in the blood vessel 312.

Accordingly, as shown in FIG. 4, the blood glucose measurement apparatus 100 may determine the blood glucose level of the user by subtracting a larger correction value from a measured value of the glucose concentration 490 in the interstitial fluid 334 when a rate of decrease of the blood glucose level of the user is larger.

The rate of change of the blood glucose level of the user may be determined based on a rate of change of the glucose concentration 490 in the interstitial fluid 334. Alternatively, the rate of change of the blood glucose level of the user may be determined based on an amount of exercise performed by the user, a time taken to consume food, calories of consumed food, whether the user is in a sleeping state, or a hormone cycle, but is not limited thereto.

Figure 5:
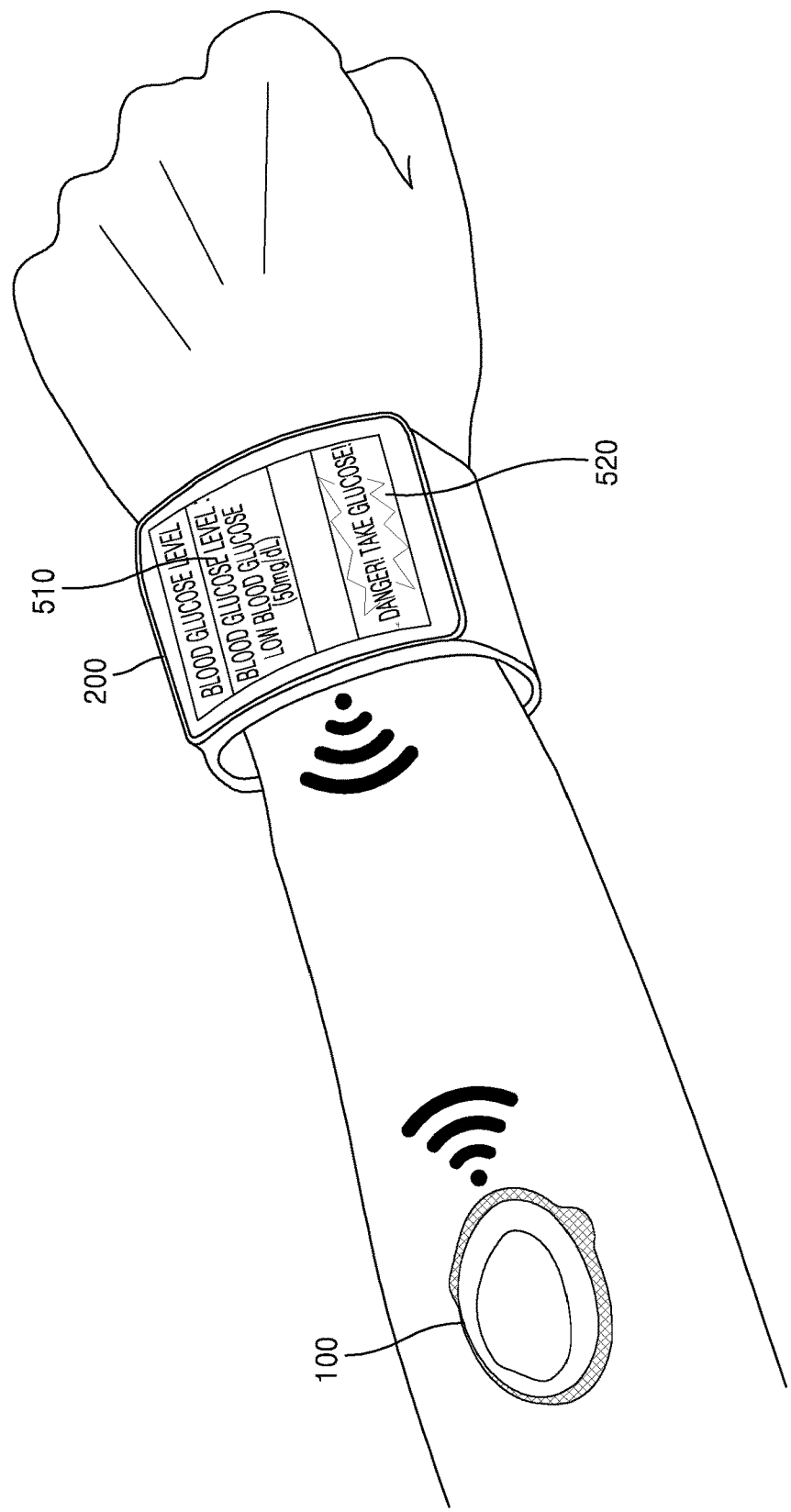
FIG. 5 is a diagram illustrating a blood glucose measurement apparatus and a device for displaying a blood glucose level, according to an embodiment of the present disclosure.

FIG. 5 is a diagram illustrating a blood glucose measurement apparatus and a device for displaying a blood glucose level, according to an embodiment of the present disclosure.

Referring to FIG. 5, the blood glucose measurement apparatus 100 has a patch shape and is attached to the skin of the user to determine a blood glucose level 510 of the user.

For example, the blood glucose measurement apparatus 100 may measure the glucose concentration in sweat secreted from the skin of the user, or may measure the glucose concentration in an interstitial fluid in the skin, and may determine the blood glucose level 510 of the user based on the measured glucose concentration.

In addition, the blood glucose measurement apparatus 100 establishes a short-distance wireless communication connection with a device 200. The blood glucose measurement apparatus 100 transmits the determined blood glucose level 510 of the user to the device 200 by using the established short-distance wireless communication connection. Aside from the blood glucose level 510 of the user, the blood glucose measurement apparatus 100 may also transmit the measured glucose concentration and the rate of change of the glucose concentration to the device 200. The device 200 displays the blood glucose level 510 of the user, which has been received from the blood glucose measurement apparatus 100. When the received blood glucose level 510 of the user is less than or greater than a reference blood glucose level range, the device 200 displays a warning message 520 indicating low blood glucose or high blood glucose. The reference blood glucose level range may indicate a normal blood glucose level range of a normal person. For example, the reference blood glucose level range may be 80 through 160 mg/dL.

In addition, the blood glucose measurement apparatus 100 may include a movement sensor, a temperature sensor, an electrocardiogram (ECG) sensor, a photoelectric plethysmography (PPG) sensor, a galvanic skin response (GSR) sensor, or a passometer. The blood glucose measurement apparatus 100 may acquire information about an amount of exercise performed by the user, a body temperature, whether the user is in a sleeping state, a hormone cycle, or a heart rate through the sensor. The blood glucose measurement apparatus 100 may determine whether a rate of change of a blood glucose level of the user has changed, whether the rate of change of the blood glucose level of the user exceeds a preset rate of change, or the rate of change of the blood glucose level of the user, based on the acquired information about an amount of exercise performed by the user, a body temperature, whether the user is in the sleeping state, a hormone cycle, or a heart rate.

According to an embodiment of the present disclosure, the blood glucose measurement apparatus 100 may receive information about an amount of exercise performed by the user, a body temperature, whether the user is in the sleeping state, a hormone cycle, or a heart rate from the device 200, through the short-distance wireless communication connection. The blood glucose measurement apparatus 100 may determine whether a rate of change of a blood glucose level of the user has changed, whether the rate of change of the blood glucose level of the user exceeds a preset rate of change, or the rate of change of the blood glucose level of the user, based on the received information about an amount of exercise performed by the user, a body temperature, whether the user is in the sleeping state, a hormone cycle, or a heart rate.

Figure 6:
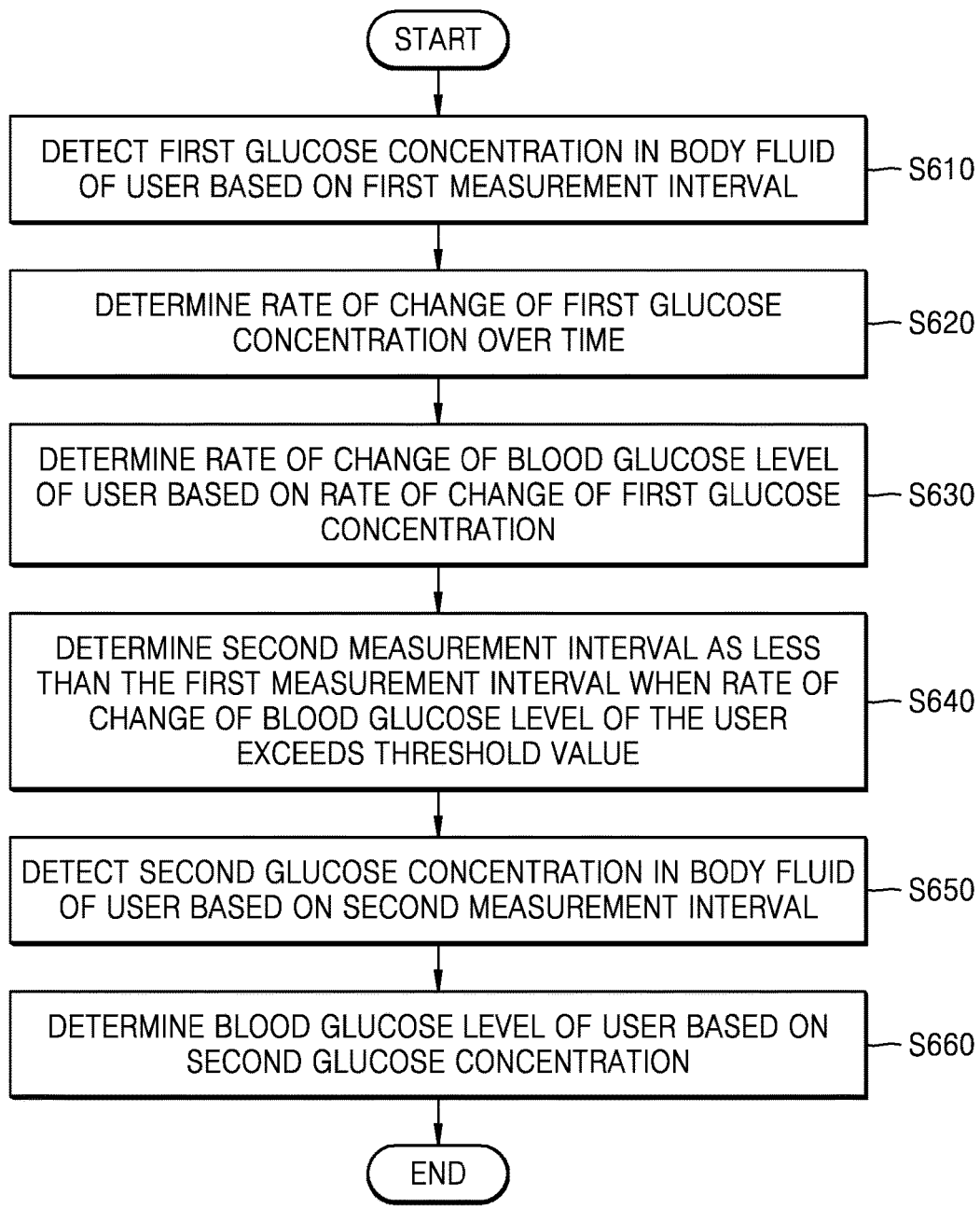
FIG. 6 is a flowchart illustrating a method by which a blood glucose measurement apparatus determines a blood glucose level of a user based on a rate of change of measured glucose concentration, according to an embodiment of the present disclosure.

FIG. 6 is a flowchart illustrating a method by which the blood glucose measurement apparatus determines a blood glucose level of a user based on a rate of change of the measured glucose concentration, according to an embodiment of the present disclosure.

In step S610, the blood glucose measurement apparatus 100 detects a first glucose concentration in a body fluid of the user based on the first measurement interval. Step S610 is described in greater detail above with respect to step S210 of FIG. 2A.

In step S620, the blood glucose measurement apparatus 100 determines a rate of change of the first glucose concentration over time.

In step S630, the blood glucose measurement apparatus 100 determines a rate of change of a blood glucose level of the user based on the rate of change of the first glucose concentration.

For example, the blood glucose measurement apparatus 100 may determine the rate of change of the first glucose concentration as the rate of change of the blood glucose level of the user. In another example, the blood glucose measurement apparatus 100 may determine the rate of change of the first glucose concentration as a rate of change of a blood glucose level of the user prior to a certain time. In another example, the blood glucose measurement apparatus 100 may determine a value obtained by adding a correction value to the rate of change of the first glucose concentration as the rate of change of the blood glucose level of the user. In this case, the correction value may be determined to be larger when the rate of change of the first glucose concentration is larger. Correction values may be stored in advance in the blood glucose measurement apparatus 100 with respect to rates of change of glucose concentration.

In step S640, the blood glucose measurement apparatus 100 determines a value that is less than the first measurement interval, as the second measurement interval, when the rate of change of the blood glucose level of the user exceeds the threshold value. In step S650, the blood glucose measurement apparatus 100 detects a second glucose concentration in the body fluid based on the determined second measurement interval. In step S660, the blood glucose measurement apparatus 100 determines the blood glucose level of the user based on the second glucose concentration. Steps S640 through S660 are described in greater detail above with reference to steps S230 through S250 of FIG. 2A.

Figure 7:
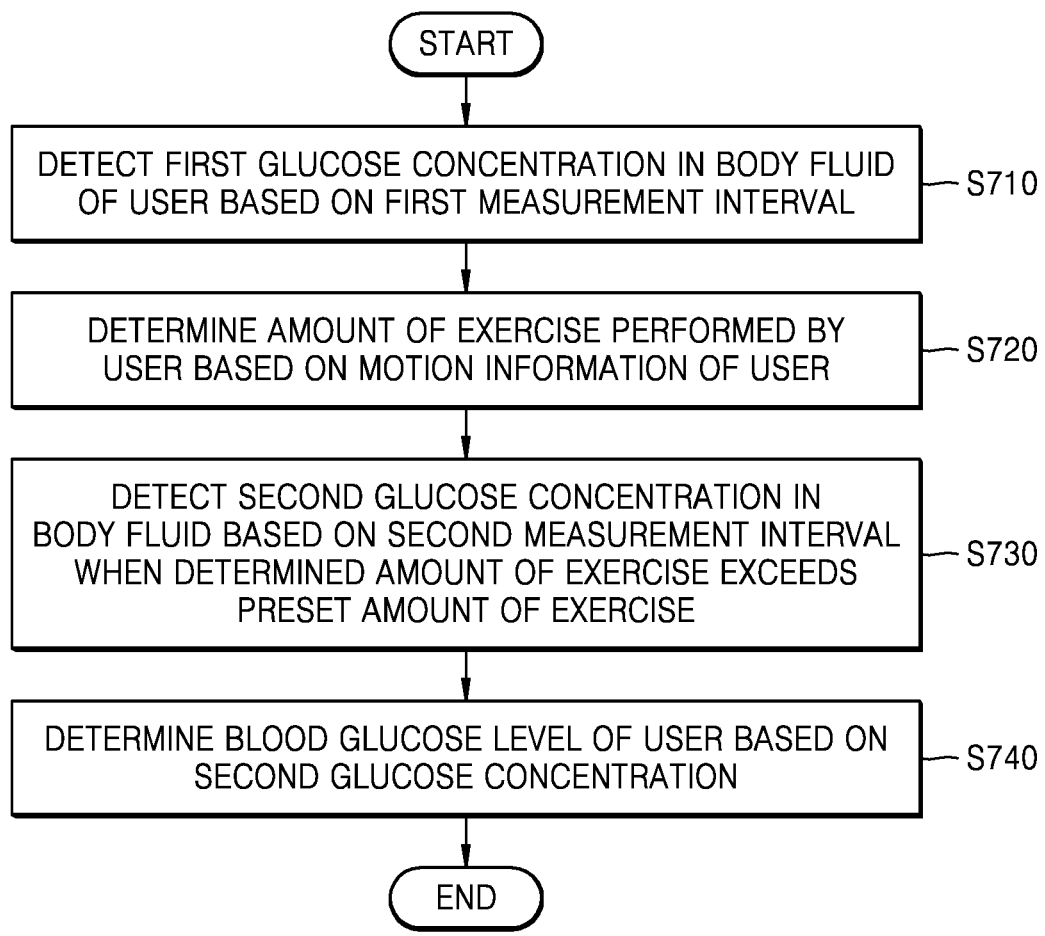
FIG. 7 is a flowchart illustrating a method by which a blood glucose measurement apparatus determines a blood glucose level of a user based on an amount of exercise performed by the user, according to an embodiment of the present disclosure.

FIG. 7 is a flowchart illustrating a method by which the blood glucose measurement apparatus determines a blood glucose level of a user based on an amount of exercise performed by the user, according to an embodiment of the present disclosure.

In step S710, the blood glucose measurement apparatus 100 detects a first glucose concentration in a body fluid of the user based on the first measurement interval. Step S710 is described in greater detail above with reference to step S210 of FIG. 2A.

In step S720, the blood glucose measurement apparatus 100 determines an amount of exercise performed by the user based on motion information of the user.

For example, the blood glucose measurement apparatus 100 may receive the motion information of the user from a movement sensor attached to the user.

The movement sensor may include a global positioning system (GPS) sensor, a motion sensor, an acceleration sensor, and an ECG sensor, but is not limited thereto. The motion information may include information on whether the user is walking, running, staying in place, or moving in place. In addition, the motion information may include a moving speed of the user or a moving time.

Alternatively, the blood glucose measurement apparatus 100 may receive motion information of the user from a movement sensor provided in the blood glucose measurement apparatus 100. Alternatively, the blood glucose measurement apparatus 100 may receive motion information of the user from the device 200 separately attached to the user.

The blood glucose measurement apparatus 100 may calculate an amount of exercise performed by the user based on the motion information of the user. The amount of exercise performed by the user may indicate an amount of exercise performed by the user, and may be expressed by an amount of calories consumed during the exercise. For example, the amount of exercise may be calculated by exercise intensity× time and may have a unit of Kcal.

The blood glucose measurement apparatus 100 may receive an acceleration of the user over time from the acceleration sensor, determine a pattern of the received acceleration, and determine a moving pattern of the user based on the determined acceleration pattern. The moving pattern of the user may include, for example, whether the user is walking, running, riding a bicycle, or on a vehicle, and may be referred to as exercise intensity. Alternatively, an amount of exercise per unit time consumed during each of walking, running, and bicycle riding may be stored in the blood glucose measurement apparatus 100. In addition, the blood glucose measurement apparatus 100 may receive a moving speed and a moving distance of the user from the GPS sensor. Accordingly, the blood glucose measurement apparatus 100 may determine an amount of exercise performed by the user based on the moving pattern, the moving speed, and the moving distance of the user.

Alternatively, the blood glucose measurement apparatus 100 may receive information about a motion performed by the user from the motion sensor. The information about a motion may include a motion of the arms, a motion of the legs, and a motion of the torso, but is not limited thereto. The blood glucose measurement apparatus 100 may determine a weight training action of the user from the information about a motion. The blood glucose measurement apparatus 100 may store, in advance, information about a motion of the user according to the performance of each weight training action. In addition, the blood glucose measurement apparatus 100 may store an amount of exercise per unit time according to the performance of each weight training action. Accordingly, the blood glucose measurement apparatus 100 may determine a weight training action performed by the user based on the received information about a motion, and may determine an amount of exercise over time based on the determined action and an action time.

Alternatively, the blood glucose measurement apparatus 100 may receive information about a heart rate of the user from the ECG sensor attached to the user, and may determine a blood glucose level of the user based on the received information about a heart rate. For example, the blood glucose measurement apparatus 100 may store amounts of exercise per unit time based on heart rates. Accordingly, the blood glucose measurement apparatus 100 may determine an amount of exercise based on the received heart rate.

In step S730, the blood glucose measurement apparatus 100 may detect a second glucose concentration in the body fluid based on the second measurement interval, when the determined amount of exercise performed by the user exceeds a preset amount of exercise.

Muscles obtain energy from glycogen in an initial stage of exercise, but when glycogen in the muscles is lacking due to a long exercise time, the muscles obtain energy from glucose. Therefore, along with a long exercise time or an increased exercise intensity, an amount of glucose in the blood, which is absorbed into the muscles, may also increase. In addition, even after the exercise, insulin sensitivity of the user may increase, thereby continuously absorbing glucose in the blood. Therefore, during and after the exercise, the blood glucose level of the user may decrease. Generally, it may be considered that the blood glucose level of the user decreases during an exercise and for two hours after the exercise.

Accordingly, the blood glucose measurement apparatus 100 may change the glucose concentration measurement interval to the second measurement interval as soon as the user begins an exercise. Alternatively, the blood glucose measurement apparatus 100 may change the glucose concentration measurement interval to the second measurement interval when an exercise is maintained for a time that exceeds a preset time.

In addition, the blood glucose measurement apparatus 100 may gradually reduce the glucose concentration measurement interval in proportion to the intensity of an exercise.

In addition, the blood glucose measurement apparatus 100 may determine the second measurement interval to be a shorter time interval as an amount of exercise performed by the user further increases. For example, the blood glucose measurement apparatus 100 may decrease the second measurement interval as an exercise time of the user increases. Alternatively, the blood glucose measurement apparatus 100 may decrease the second measurement interval as the intensity of exercise performed by the user increases.

In addition, the blood glucose measurement apparatus 100 may determine that the blood glucose level of the user decreases, based on an exercise start time and a time that the exercise is maintained, and may determine a reduction rate of the blood glucose level of the user based on a time that the exercise is maintained or the intensity of an exercise.

For example, the blood glucose measurement apparatus 100 may determine that the reduction rate of the blood glucose level of the user increases as soon as the user starts an exercise. Alternatively, the blood glucose measurement apparatus 100 may determine that the reduction rate of the blood glucose level of the user increases when an exercise is maintained for a time that exceeds a preset time. For example, the blood glucose measurement apparatus 100 may determine that the blood glucose level of the user starts to decrease after 10 minutes elapses since starting an exercise at a reference intensity, and a reduction speed of the blood glucose level of the user increases according to the continuation of the exercise. In addition, the blood glucose measurement apparatus 100 may determine that the reduction speed of the blood glucose level of the user increases in proportion to the intensity of the exercise. In addition, the blood glucose measurement apparatus 100 may determine that the blood glucose level of the user decreases for two hours after ending the exercise and the reduction speed decreases.

The blood glucose measurement apparatus 100 may determine the second measurement interval based on the determined reduction rate or increase rate of the blood glucose level.

The blood glucose measurement apparatus 100 may detect a second glucose concentration in the body fluid based on the determined second measurement interval.

In step S740, the blood glucose measurement apparatus 100 determines the blood glucose level of the user based on the second glucose concentration. Step S740 is described in greater detail above with reference to step S250 of FIG. 2A.

Figure 8:
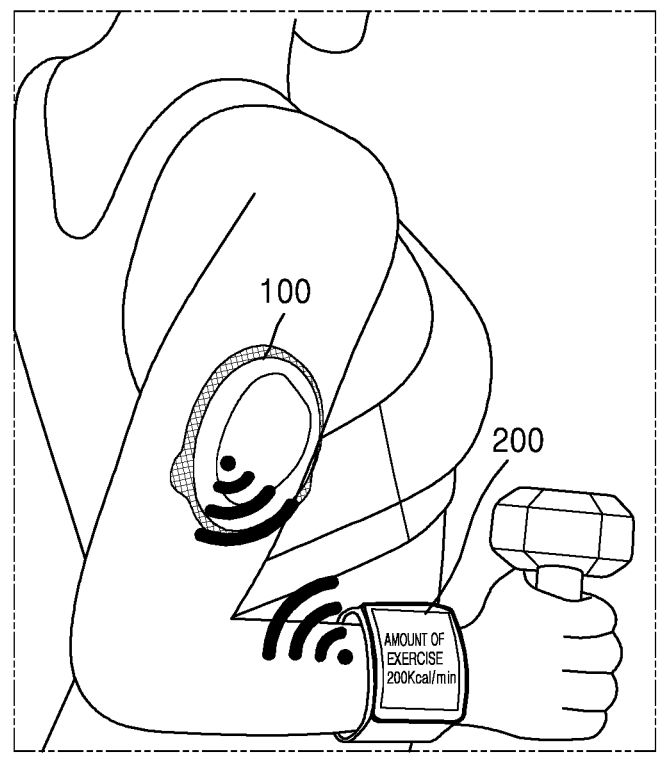
FIG. 8 is a diagram illustrating a method by which a blood glucose measurement apparatus determines a rate of change of a blood glucose level of a user based on an amount of exercise performed by the user, according to an embodiment of the present disclosure.

FIG. 8 is a diagram illustrating a method by which the blood glucose measurement apparatus determines a rate of change of a blood glucose level of a user based on an amount of exercise performed by the user, according to an embodiment of the present disclosure.

Referring to FIG. 8, the blood glucose measurement apparatus 100 receives information about an amount of exercise from the device 200, and determines the rate of change of the blood glucose level of the user based on the received amount of exercise performed by the user.

The device 200 includes a movement sensor. The movement sensor may include at least one of a GPS sensor, a motion sensor, an acceleration sensor, and an ECG sensor, but is not limited thereto. The device 200 may determine an amount of exercise performed by the user using the movement sensor.

In addition, the blood glucose measurement apparatus 100 receives information about whether an event has occurred from the device 200 through a short-distance wireless communication connection.

For example, the device 200 transmits information about an amount of exercise performed by the user to the blood glucose measurement apparatus 100 when the amount of exercise performed by the user exceeds a preset reference. The information about an amount of exercise performed by the user may include information indicating that the amount of exercise performed by the user has exceeded the preset reference and a calculated amount of exercise performed by the user. In addition, when the amount of exercise performed by the user is less than a preset amount of exercise, the device 200 transmits information indicating that the event has ended to the blood glucose measurement apparatus 100.

When information indicating that an event has occurred is received from the device 200, the blood glucose measurement apparatus 100 changes the glucose concentration measurement interval based on the received information.

Figure 9A:
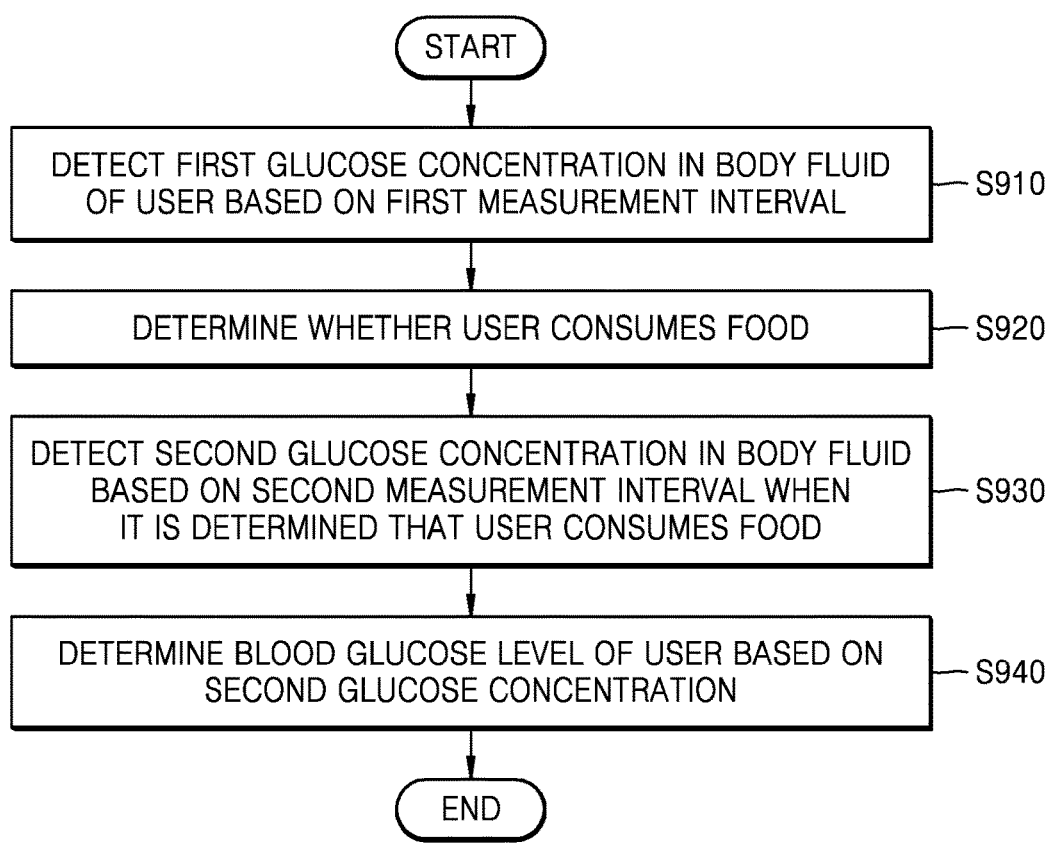
FIG. 9A is a flowchart illustrating a method by which a blood glucose measurement apparatus determines a rate of change of a blood glucose level of a user based on information about food consumed by the user, according to an embodiment of the present disclosure.

FIG. 9A is flowchart illustrating a method by which the blood glucose measurement apparatus determines a rate of change of a blood glucose level of a user based on whether the user consumes food, according to an embodiment of the present disclosure.

In step S910, the blood glucose measurement apparatus 100 detects a first glucose concentration in a body fluid of the user based on the first measurement interval. Step S910 is described in greater detail above with respect to step S210 of FIG. 2A.

In step S920, the blood glucose measurement apparatus 100 determines whether the user consumes food.

For example, the blood glucose measurement apparatus 100 may display a user interface for inputting a meal start time or a meal end time, and may receive a user input of inputting a meal start time or a meal end time through the user interface. When a meal start time is input, the blood glucose measurement apparatus 100 determines that the user starts to consume food, and when a meal end time is input, the blood glucose measurement apparatus 100 may determine that the user stops consuming food.

In another example, the blood glucose measurement apparatus 100 may provide a user interface for setting a meal time, and may determine that the user consumes food during the preset meal time.

In another example, the blood glucose measurement apparatus 100 may determine whether the user is consuming food by using an olfactory sensor attached to the blood glucose measurement apparatus 100 or another device of the user. In this case, when the olfactory sensor recognizes a food smell, the blood glucose measurement apparatus 100 may determine that the user is taking food.

In addition, the blood glucose measurement apparatus 100 may acquire information about food taken by the user. The information about food may include information about a food consumption time of the user, types of the consumed food, and calories, but is not limited thereto. The blood glucose measurement apparatus 100 may display a user interface for inputting information about food and directly receive the information about food from the user through the displayed user interface. Alternatively, the blood glucose measurement apparatus 100 may receive information about food from a separate device.

In step S930, the blood glucose measurement apparatus 100 detects a second glucose concentration in a body fluid based on the second measurement interval, when it is determined that the user is consuming food.

Figure 9B:
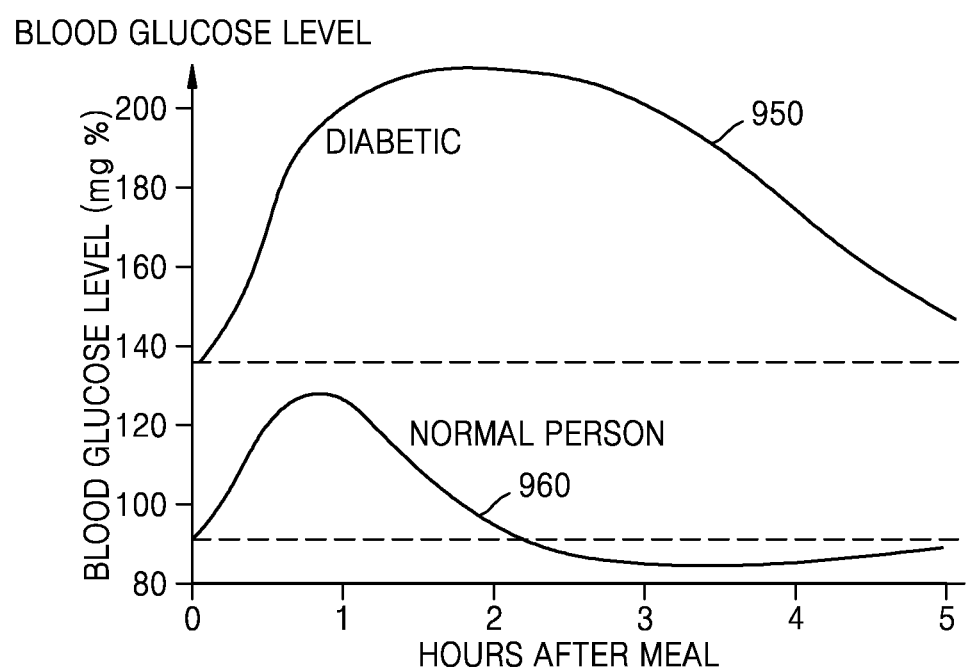
FIG. 9B is a graph showing a change in a blood glucose level over time after consuming food, according to an embodiment of the present disclosure.

FIG. 9B is a graph showing a change in a blood glucose level over time after consuming food, according to an embodiment of the present disclosure. Referring to FIG. 9B, after starting to consume food, a blood glucose level of a user increases, and after a certain time elapses, the blood glucose level of the user decreases.

A graph 950 shows that a blood glucose level of a diabetic increases for about two hours after a meal and gradually decreases thereafter. A graph 960 shows that a blood glucose level of a normal person increases for about one hour after a meal and decreases thereafter, thereby maintaining fasting blood glucose.

As shown in FIG. 9B, based on the fact that a blood glucose level of a user sharply changes for one or two hours after a meal, the blood glucose measurement apparatus 100 may determine that a rate of change of the blood glucose level of the user is a preset rate of change or more for one or two hours after a meal.

In addition, when it is determined that the user is consuming food, the blood glucose measurement apparatus 100 may change the blood glucose measurement interval. For example, the blood glucose measurement apparatus 100 may change the blood glucose measurement interval to the second measurement interval, which is shorter than the first measurement interval, from a time the user starts a meal. The second measurement interval may be preset in the blood glucose measurement apparatus 100 based on food intake. In addition, when two hours elapses after the meal, the blood glucose measurement apparatus 100 may change the blood glucose measurement interval from the second measurement interval back to the first measurement interval.

In addition, according to consumed food, a peak value or a rate of change of a blood glucose level may vary. For example, when bread is mainly consumed, the peak value or the rate of change of the blood glucose level may increase. When brown rice is mainly consumed, the peak value or the rate of change of the blood glucose level may decrease. Accordingly, the blood glucose measurement apparatus 100 may determine the rate of change of the blood glucose level of the user based on food consumed by the user. In addition, the blood glucose measurement apparatus 100 may determine the blood glucose measurement interval based on food consumed by the user. The influence that each type of food has on increasing a rate of a blood glucose level may be stored as a numeric value, and the blood glucose measurement apparatus 100 may determine the blood glucose measurement interval based on the influence that the food consumed by the user has on increasing the rate of a blood glucose level and an amount of the consumed food.

Referring back to FIG. 9A, in step S940, the blood glucose measurement apparatus 100 determines the blood glucose level of the user based on the glucose concentration detected in the second measurement interval. Step S940 is described in greater detail above with respect to step S250 of FIG. 2A.

Figure 10A:
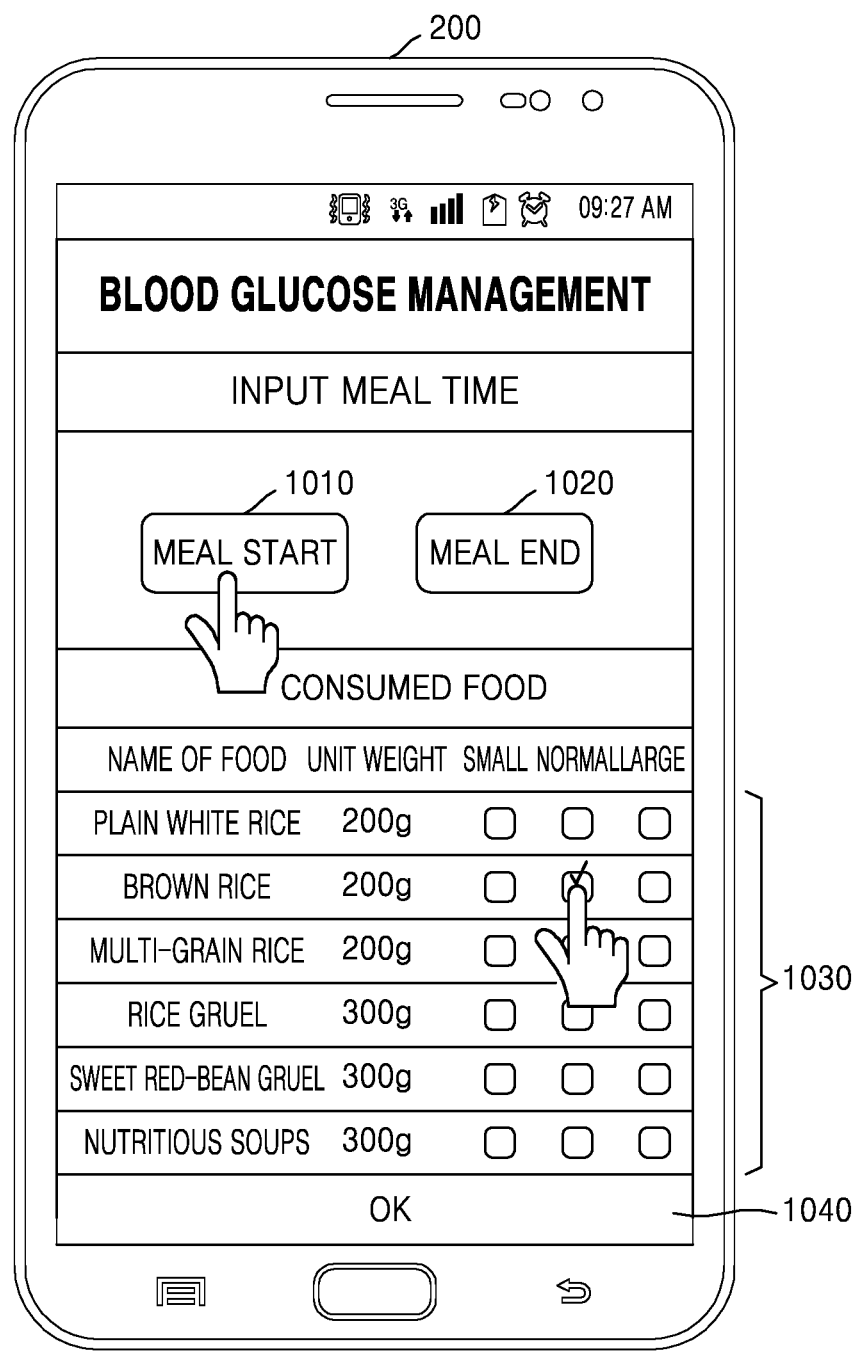
FIG. 10A is a diagram illustrating a user interface for inputting information about food consumed by a user, according to an embodiment of the present disclosure.

FIG. 10A is a diagram illustrating a user interface for inputting information about food consumed by a user, according to an embodiment of the present disclosure.

Referring to FIG. 10A, the blood glucose measurement apparatus 100 receives information about food consumed by the user from the device 200, and the device 200 provides the user interface for inputting the information about food consumed by the user.

The user interface for inputting the information about food consumed by the user includes buttons 1010 and 1020 for inputting a meal time and check boxes 1030 for selecting consumed food.

When a user input selecting the meal start button 1010 is received, the device 200 transmits, to the blood glucose measurement apparatus 100, a time the meal start button 1010 was selected as a time the user started to consume food. In addition, when a user input selecting the meal end button 1020 is received, the device 200 transmits, to the blood glucose measurement apparatus 100, a time the meal end button 1020 was selected as a time the user stops consuming food. When the meal start time is received from the device 200, the blood glucose measurement apparatus 100 determines that a blood glucose level of the user sharply increases after a certain time from the meal start time. In addition, when the meal end time is received from the device 200, the blood glucose measurement apparatus 100 determines that the blood glucose level of the user decreases after a certain time from the meal end time.

In addition, the device 200 displays the check boxes 1030 for inputting information identifying food consumed by the user and an amount of the consumed food.

When a user input of pushing an "OK" button 1040 is received after inputting consumed food and an amount of the consumed food, the device 200 calculates calories consumed by the user based on calories absorbed inside the body per unit weight with respect to the selected food and an amount of the consumed food. Thereafter, the device 200 transmits the calculated calories to the blood glucose measurement apparatus 100.

Figure 10B:
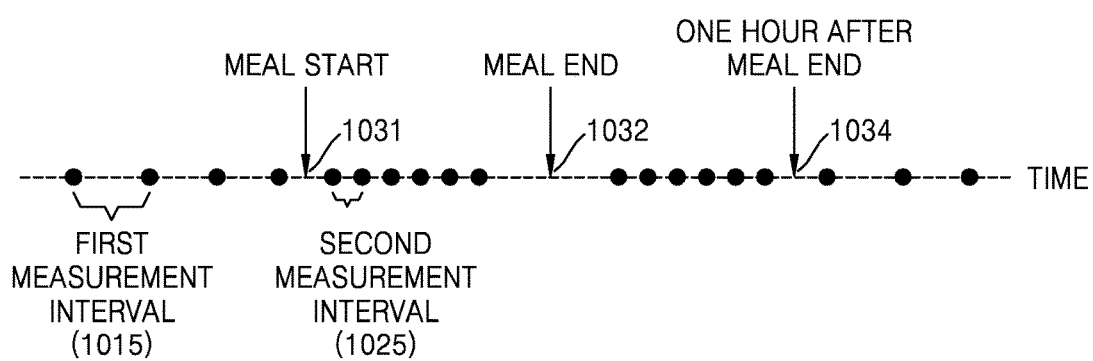
FIG. 10B is a time table illustrating a method by which a blood glucose measurement apparatus changes a glucose concentration measurement interval when a user consumes food, according to an embodiment of the present disclosure.

FIG. 10B is a time table showing a method by which the blood glucose measurement apparatus changes the glucose concentration measurement interval when a user consumes food, according to an embodiment of the present disclosure.

Referring to FIG. 10B, when the user consumes food, the blood glucose measurement apparatus 100 changes the glucose concentration measurement interval.

When the user selects the meal start button 1010 displayed on the device 200 of FIG. 10A, the blood glucose measurement apparatus 100 receives, from the device 200, information indicating that the user started a meal and a meal start time.

When the information indicating that the user has started a meal is received, the blood glucose measurement apparatus 100 changes the glucose concentration measurement interval from a first measurement interval 1015 to a second measurement interval 1025. Accordingly, after a meal start time 1031, the blood glucose measurement apparatus 100 measures glucose concentrations more frequently than before.

When the user selects the meal end button 1020 displayed on the device 200 of FIG. 10A, the blood glucose measurement apparatus 100 receives, from the device 200, information indicating that the user has ended a meal and a meal end time.

When the information indicating that the user ended a meal is received, the blood glucose measurement apparatus 100 changes the glucose concentration measurement interval from the second measurement interval 1025 back to the first measurement interval 1015 at a time point 1034 after a preset time elapses from a meal end time 1032. Accordingly, after the time point 1034, the blood glucose measurement apparatus 100 measures glucose concentrations less frequently than before.

Figure 11:
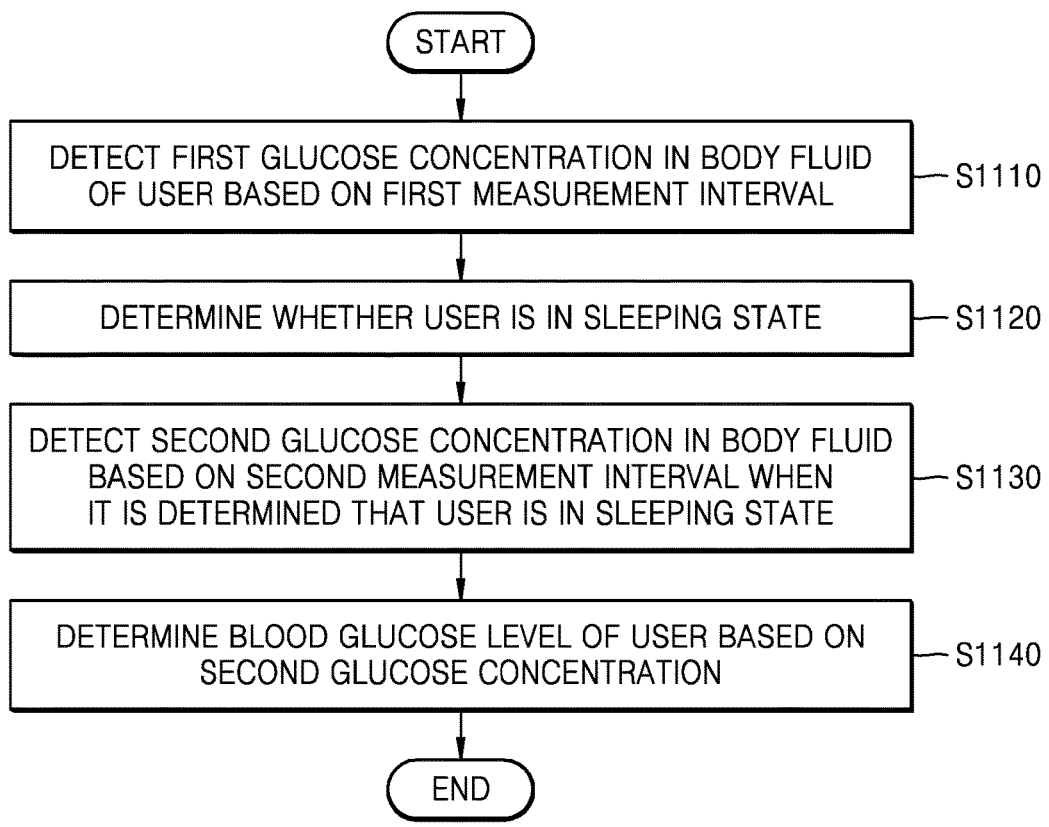
FIG. 11 is a flowchart illustrating a method by which a blood glucose measurement apparatus determines a rate of change of a blood glucose level of a user based on a sleeping state of the user, according to an embodiment of the present disclosure.

FIG. 11 is a flowchart illustrating a method by which the blood glucose measurement apparatus determines a rate of change of a blood glucose level of a user based on a sleeping state of the user, according to an embodiment of the present disclosure.

In step S1110, the blood glucose measurement apparatus 100 detects a first glucose concentration in a body fluid of the user based on the first measurement interval. Step S1110 is described in greater detail above with reference to step S210 of FIG. 2A.

In step S1120, the blood glucose measurement apparatus 100 determines whether the user is in a sleeping state.

Generally, a heart rate of the user during sleeping is about 10 beats per minute less than a heart rate of the user while the user is awake. Accordingly, the blood glucose measurement apparatus 100 may receive a heart rate of the user from a heartbeat sensor attached to the user, and may determine whether the user is in the sleeping state based on the received heart rate.

Alternatively, heart rate variability of the user during sleeping generally has a low value. Accordingly, the blood glucose measurement apparatus 100 may receive information about a heart rate of the user from the heartbeat sensor, calculate heart rate variability based on the received information about the heart rate, and determine whether the user is in the sleeping state based on the calculated heart rate variability.

In step S1130, the blood glucose measurement apparatus 100 detects a second glucose concentration in the body fluid based on the second measurement interval, when it is determined that the user is in the sleeping state.

A blood glucose level of normal people may decrease while sleeping. Accordingly, when the user is in the sleeping state, the blood glucose measurement apparatus 100 may determine that the rate of change of the blood glucose level of the user increases. In addition, when the user is in the sleeping state, the blood glucose measurement apparatus 100 may change the glucose concentration measurement interval to the second measurement interval, which is shorter than the first measurement interval, and may detect the glucose concentration in the body fluid based on the changed second measurement interval. The second measurement interval may be preset in the blood glucose measurement apparatus 100 in correspondence with the sleeping state.

In step S1140, the blood glucose measurement apparatus 100 determines the blood glucose level of the user based on the second glucose concentration. Step S1140 is described in greater detail above with respect to step S250 of FIG. 2A.

In addition, the blood glucose measurement apparatus 100 may determine whether the user awakens from the sleeping state. When the user is out of the sleeping state, the blood glucose measurement apparatus 100 may change the glucose concentration measurement interval from the second measurement interval back to the first measurement interval.

Figure 12A:
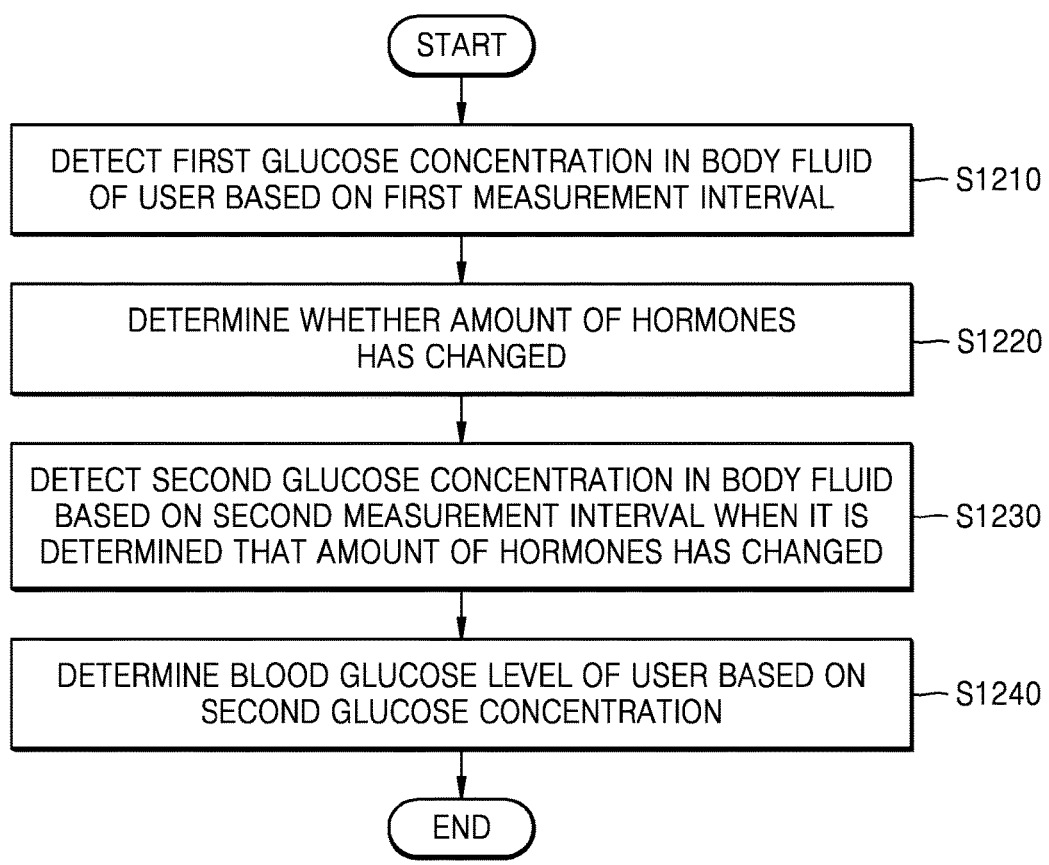
FIG. 12A is a flowchart illustrating a method by which a blood glucose measurement apparatus determines a rate of change of a blood glucose level of a user based on a hormone cycle of the user, according to an embodiment of the present disclosure.

FIG. 12A is a flowchart illustrating a method by which the blood glucose measurement apparatus determines a rate of change of a blood glucose level of a user based on a hormone cycle of the user, according to an embodiment of the present disclosure.

In step S1210, the blood glucose measurement apparatus 100 detects a first glucose concentration in a body fluid of the user based on the first measurement interval. Step S1210 is described in greater detail above with respect to step S210 of FIG. 2A.

In step S1220, the blood glucose measurement apparatus 100 determines whether an amount of hormones has changed.

The hormones may indicate chemical substances secreted from one part of the body and moving to a target organ with the blood. The hormones may include estrogen, progesterone, a growth stimulating hormone, and the like, but are not limited thereto.

Most hormones in the body tend to change a body temperature. Accordingly, the blood glucose measurement apparatus 100 may determine an amount of hormones in the body of the user based on a body temperature of the user. Body temperatures depending on amounts of hormones in the body may be stored in advance in the blood glucose measurement apparatus 100. Accordingly, the blood glucose measurement apparatus 100 may receive information about a body temperature of the user from a temperature sensor, and may determine an amount of hormones in the body of the user based on the received information.

Figure 12B:
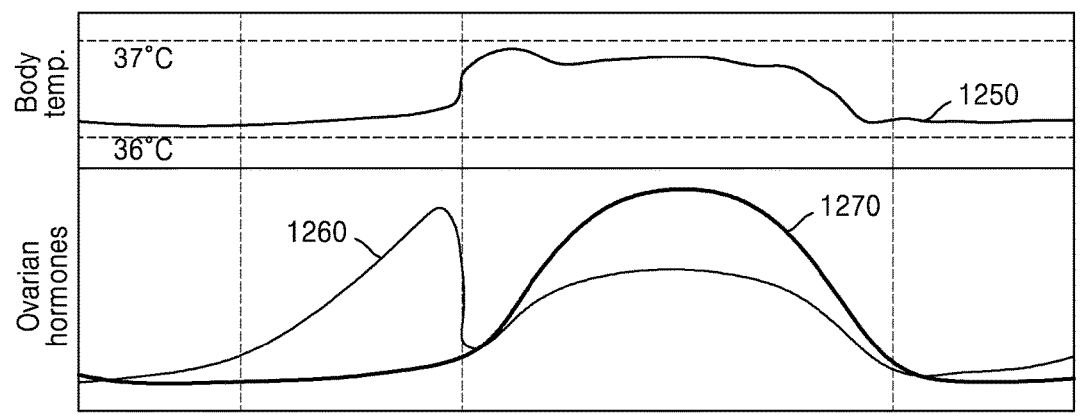
FIG. 12B is a body temperature variation graph, an estrogen variation graph, and a progesterone variation graph over a time interval during a woman's menstruation cycle.

FIG. 12B is a diagram illustrating a body temperature variation graph 1250, an estrogen variation graph 1260, and a progesterone variation graph 1270 over time during a woman's menstruation cycle.

Referring to FIG. 12B, when a value of estrogen drops from a peak value, a body temperature may increase by about 1° C. In addition, when a value of progesterone increases and then decreases, the body temperature may decrease by about 1° C. Accordingly, the blood glucose measurement apparatus 100 may determine that a value of estrogen drops from the peak value when the body temperature increases, and may determine that a value of progesterone decreases from a peak value when the body temperature decreases.

Alternatively, the blood glucose measurement apparatus 100 may acquire a hormone cycle of the user, and may determine an amount of hormones in the body of the user based on the acquired hormone cycle.

The amount of hormones in the body may periodically repeat. For example, an amount of progesterone and estrogen may repeat during a woman's menstruation cycle. In another example, a secretion amount of a growth hormone increases during the night. Particularly, the secretion amount of the growth hormone may be greatest between nine o'clock and eleven o'clock at night.

Accordingly, the blood glucose measurement apparatus 100 may measure a change in a body temperature during a plurality of cycles, and may determine the hormone cycle of the user based on the measured temperature change.

Alternatively, according to an embodiment of the present disclosure, the blood glucose measurement apparatus 100 may acquire a hormone increase/decrease cycle input by the user. For example, the separate device 200 may receive a user input inputting a menstruation start date and a menstruation end date, and may determine the user's menstruation cycle based on the received menstruation start date and menstruation end date. In addition, the device 200 may determine the hormone increase/decrease cycle of the user based on the determined user's menstruation cycle, and may transmit a change in hormones at a certain time point to the blood glucose measurement apparatus 100 based on the determined hormone increase/decrease cycle.

Referring back to FIG. 12A, in step S1230, the blood glucose measurement apparatus 100 detects a second glucose concentration in the body fluid based on the second measurement interval, when it is determined that the amount of hormones has changed.

A blood glucose level of the user may vary depending on an increase/decrease in hormones in the body.

For example, a blood glucose level of some women may increase beginning several days before starting menstruation, and when menstruation starts, the increased blood glucose level may drop to a normal blood glucose level. However, a blood glucose level of some other women may increase several days before starting menstruation, and even after menstruation starts, the increased blood glucose level may continue for several days.

An increase/decrease of a blood glucose level appearing in each stage of a menstruation cycle may vary depending on the person, but an increase/decrease of a blood glucose level through a menstruation cycle may have a similar pattern for each person. This may occur since a level change in estrogen and progesterone occurring during a menstruation cycle temporarily increases insulin resistance. For example, progesterone may increase insulin resistance and decrease insulin sensitivity.

When it is determined that the amount of hormones has changed, the blood glucose measurement apparatus 100 may change the glucose concentration measurement interval from the first measurement interval to the second measurement interval, which is shorter than the first measurement interval while the amount of hormones changes.

In addition, the blood glucose measurement apparatus 100 may determine a rate of change of a blood glucose level of the user based on the hormone cycle of the user. For example, the blood glucose measurement apparatus 100 may determine that the rate of change of the blood glucose level of the user increases during a progesterone increase or decrease duration, and may change the glucose concentration measurement interval.

In step S1240, the blood glucose measurement apparatus 100 determines the blood glucose level of the user based on the second glucose concentration. Step S1240 is described in greater detail above with respect to step S250 of FIG. 2A.

Figure 13A:
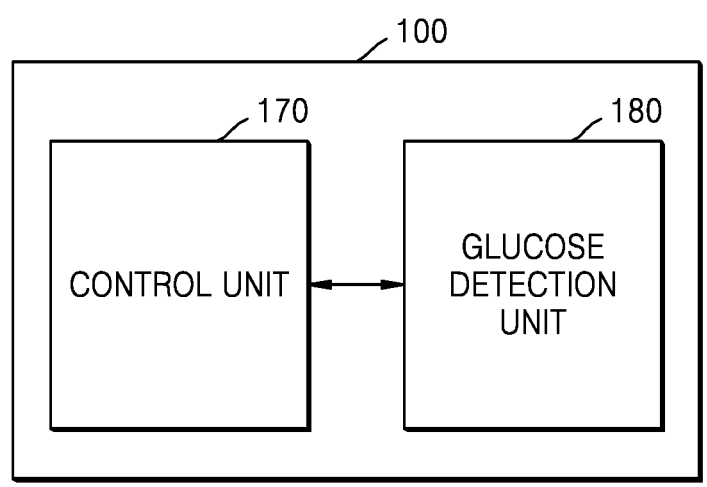
FIG. 13A is a block diagram illustrating a blood glucose measurement apparatus, according to an embodiment of the present disclosure.

FIG. 13A is a block diagram illustrating a blood glucose measurement apparatus, according to an embodiment of the present disclosure.

Referring to FIG. 13A, a blood glucose measurement apparatus 100 includes a control unit 170 and a glucose detection unit 180.

The glucose detection unit 180 may detect a glucose concentration in a body fluid of a user.

The body fluid may include at least one of an interstitial fluid, sweat, tears, and saliva. The glucose detection unit 180 may include a glucose oxidizing enzyme. In addition, the glucose detection unit 180 may include a current amount detection unit for detecting an amount of a current generated when glucose in the body fluid of the user is oxidized by means of the glucose oxidizing enzyme.

The control unit 170 may determine a rate of change of a blood glucose level of the user.

For example, the control unit 170 may determine a rate of change of the detected glucose concentration over time, which has been detected based on the first measurement interval, and may determine the rate of change of the blood glucose level of the user based on the determined rate of change of glucose concentration.

In another example, the control unit 170 may receive motion information of the user from a movement sensor attached to the user, determine an amount of exercise performed by the user based on the motion information, and determine the rate of change of the blood glucose level of the user based on the determined amount of exercise performed by the user.

In another example, the control unit 170 may acquire information about food consumed by the user, and may determine the rate of change of the blood glucose level of the user based on the acquired information about the consumed food.

In another example, the control unit 170 may determine whether the user is in a sleeping state, and may determine the rate of change of the blood glucose level of the user based on whether the user is in the sleeping state.

In another example, the control unit 170 may acquire a hormone cycle of the user, and may determine the rate of change of the blood glucose level of the user based on the acquired hormone cycle of the user.

In addition, the control unit 170 may change a measurement interval for the glucose concentration in the body fluid of the user based on the rate of change of the blood glucose level of the user.

For example, when the rate of change of the blood glucose level of the user increases while the glucose detection unit 180 detects glucose concentration in the body fluid of the user based on the first measurement interval, the control unit 170 may change the first measurement interval to the second measurement interval, which that is shorter than the first measurement interval.

In another example, when the rate of change of the blood glucose level of the user exceeds the threshold value, the control unit 170 may change the first measurement interval to the second measurement interval, which is shorter than the first measurement interval.

In addition, the control unit 170 may determine the blood glucose level of the user. For example, the control unit 170 may determine the blood glucose level of the user based on the glucose concentration in the body fluid, which has been measured by the glucose detection unit 180.

Figure 13B:
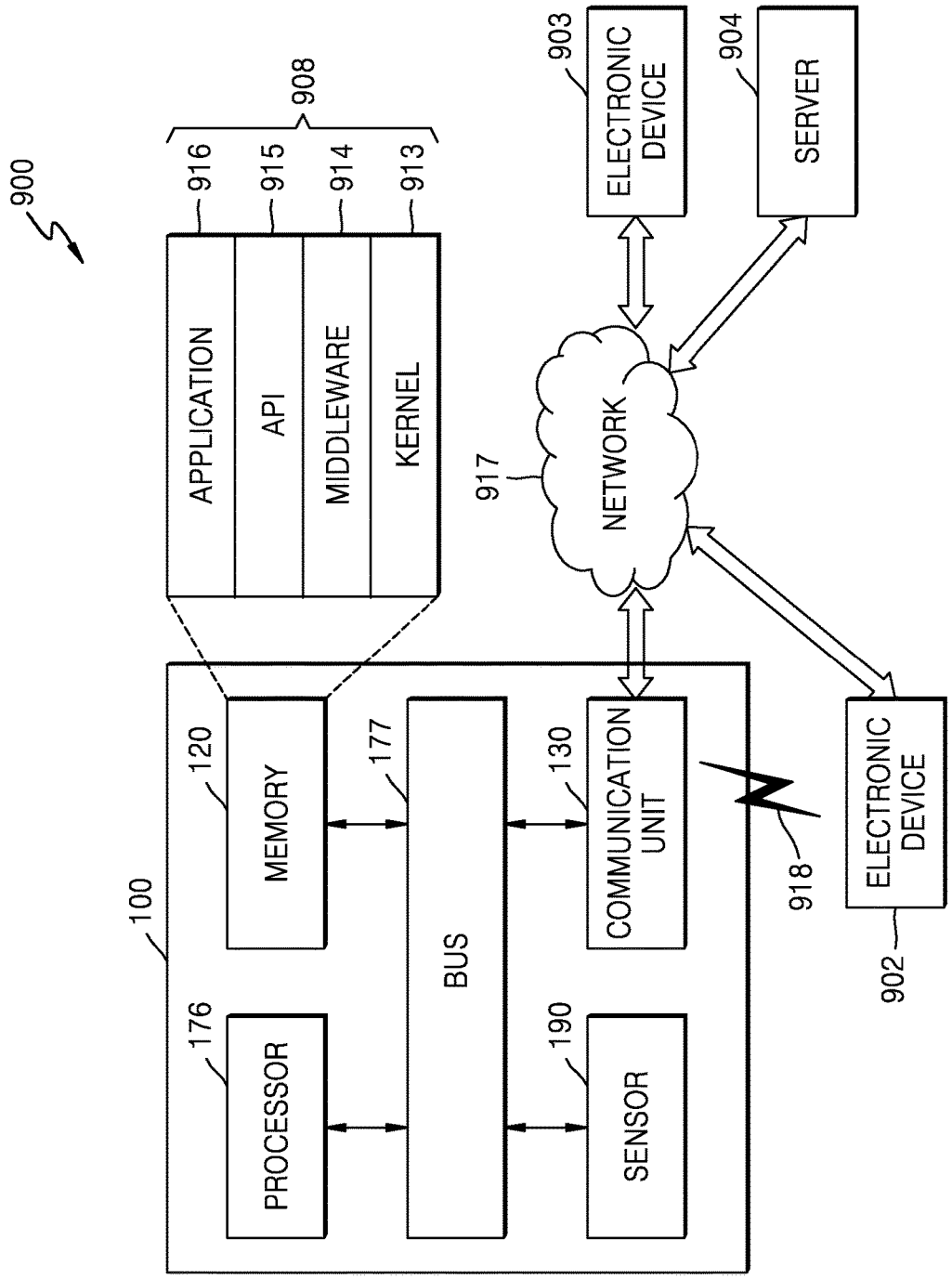
FIG. 13B is a block diagram illustrating a network environment in which the blood glucose measurement apparatus operates, according to an embodiment of the present disclosure.

FIG. 13B is a block diagram illustrating a network environment in which the blood glucose measurement apparatus 100 operates, according to an embodiment of the present disclosure.

According to an embodiment of the present disclosure, the blood glucose measurement apparatus 100 may be wearable. The blood glucose measurement apparatus 100 may be linked to various electronic devices (e.g., a first external electronic device 902, a second external electronic device 903, and a server 904.

The first external electronic device 902, the second external electronic device 903, and the server 904 may be embodied as at least one of a smartphone, a tablet personal computer (PC), a mobile phone, a video phone, an e-book reader, a desktop PC, a laptop PC, a netbook computer, a workstation, a server, a personal digital assistant (PDA), a portable multimedia player (PMP), an MP3 player, mobile medical equipment, a camera, and a wearable device (e.g., smart glasses, a head-mounted-device (HMD), electronic clothes, an electronic bracelet, an electronic necklace, an electronic appcessory, an electronic tattoo, a smart mirror, or a smart watch).

According to an embodiment of the present disclosure, the first external electronic device 902, the second external electronic device 903, and the server 904 may be embodied as a smart home appliance. The smart home appliance may include, for example, at least one of a television (TV), a digital versatile disc (DVD) player, an audio player, a refrigerator, an air conditioner, a cleaner, an oven, a microwave oven, a washing machine, an air cleaner, a set-top box, a home automation control panel, a security control panel, a TV box, a game console, an electronic dictionary, an electronic key, a camcorder, and an electronic frame.

According to an embodiment of the present disclosure, the first external electronic device 902, the second external electronic device 903, and the server 904 may be embodied as at least one of various kinds of medical equipment (e.g., various kinds of portable medical equipment (a body substance analysis device, a blood glucose meter, a heat rate meter, a blood pressure meter, and a body temperature meter), a magnetic resonance angiography (MRA) machine, a magnetic resonance imaging (MRI) machine, a computed tomography (CT) machine, and an ultrasonic machine), a navigation system, a global positioning system (GPS) receiver, an event data recorder (EDR), a flight data recorder (FDR), a car infotainment device, ship electronic equipment (e.g., a ship navigation system and a gyro compass), avionics, a security device, a vehicle head unit, an industrial or home robot, an automated teller machine (ATM) of a financial institution, a point of sales (POS) device of a store, and Internet of Things devices (IoT) (e.g., a light bulb, various kinds of sensors, an electricity or gas meter, a sprinkler device, a fire alarm, a thermostat, a streetlamp, a toaster, exercise equipment, a hot-water tank, a heater, and a boiler).

According to an embodiment of the present disclosure, the first external electronic device 902, the second external electronic device 903, and the server 904 may be embodied as at least one of furniture or a portion of a building/structure, an electronic board, an electronic signature receiving device, a projector, and various kinds of measuring devices (e.g., water, electricity, gas, and electronic wave meters). The first external electronic devices 902, the second external electronic device 903, and the server 904 may be embodied as one of various devices described above, taken alone or in combination. The first external electronic device 902, the second external electronic device 903, and the server 904 may be embodied as flexible electronic devices. In addition, the first external electronic device 902, the second external electronic device 903, and the server 904 are not limited to the devices described above and may include newly developed electronic devices.

Throughout the specification, the term "user" may indicate a person who uses the blood glucose measurement apparatus 100 or a device (e.g., an artificial intelligence blood glucose measurement apparatus) that uses the blood glucose measurement apparatus 100.

Referring back to FIG. 13B, the blood glucose measurement apparatus 100 is illustrated in a network environment 900. The blood glucose measurement apparatus 100 includes a bus 177, a processor 176, a memory 120, a communication unit 130, and a sensor 190. According to an embodiment of the present disclosure, the blood glucose measurement apparatus 100 may omit at least one of the components 120, 130, 176, and 190, or may include additional components. The processor 176 may be a central processing unit (CPU) 173 and/or a graphic processing unit (GPU) 174 shown in FIG. 14.

The bus 177 may include, for example, a circuit for connecting the components 120, 130, 176, and 190 to each other and delivering communication (e.g., a control message and/or data) between the components 120, 130, 176, and 190.

The processor 176 may include at least one of the CPE, an application processor (AP), and a communication processor (CP). For example, the processor 176 may execute control of at least one other component of the blood glucose measurement apparatus 100, perform computations related to communication, and/or perform data processing.

The memory 120 may include a volatile and/or a non-volatile memory. For example, the memory 120 may store instructions or data related to at least one other component of the blood glucose measurement apparatus 100. According to an embodiment of the present disclosure, the memory 120 may store software and/or programs 908. The programs 908 may include, for example, a kernel 913, a middleware 914, an application programming interface (API) 915, and/or an application program (or application) 916. At least some of the kernel 913, the middleware 914, and the API 915 may be named as an operating system (OS).

For example, the kernel 913 may control or manage system resources (e.g., the bus 177, the processor 176, and the memory 120) to be used to execute an operation or a function realized by other programs (e.g., the middleware 914, the API 915, and the application program 916). In addition, the kernel 913 may provide an interface capable of controlling or managing the system resources accessing individual components of the blood glucose measurement apparatus 100 through the middleware 914, the API 915, or the application program 916.

The middleware 914 may perform a relay function so that, for example, the API 915 or the application program 916 exchanges data with the kernel 913 by communicating with the kernel 913. In addition, the middleware 914 may perform control on a job request (e.g., scheduling or load balancing) by using, for example, a method of assigning a priority of using a system resource (e.g., the bus 177, the processor 176, or the memory 120) of the blood glucose measurement apparatus 100 to at least one application of the application program 916, in relation to job requests received from the application program 916.

The API 915 may include, for example, at least one of interfaces or functions (e.g., instructions) for file control, window control, image processing, character control, and the like, as an interface for the application 916 to control a function provided by the kernel 913 or the middleware 914.

The communication unit 130 may establish a connection of short-distance communication 918, such as Bluetooth (BT) or near field communication (NFC), with the first external electronic device 902. The blood glucose measurement apparatus 100 may transmit an electrical signal value due to a biomarker such as glucose, i.e., a bio-signal value, to the first external electronic device 902 through the short-distance communication 918. The first external electronic device 902 may transmit the biomarker to the second external electronic device 903 or the server 904.

In addition, the communication unit 130 may establish a communication connection between, for example, the blood glucose measurement apparatus 100 and the second external electronic device 903 or the server 904). For example, the communication unit 130 may transmit a bio-signal value obtained by measuring a detected concentration of the biomarker to the second electronic device 903 or the server 904 by connecting to a network 917 through wireless or wired communication, and communicating with the second external electronic device 903 or the server 904.

The wireless communication may use at least one of, for example, long term evolution (LTE), LTE advanced (LTE-A), code division multiple access (CDMA), wideband CDMA (WCDMA), universal mobile telecommunications system (UMTS), WiBro, and global system for mobile communications (GSM), as a cellular communication protocol. The wired communication may include at least one of, for example, universal serial bus (USB), high definition multimedia interface (HDMI), recommended standard 232 (RS-232), and plain old telephone service (POTS). The network 917 may include at least one of, for example, a telecommunication network, a computer network (e.g., local area network (LAN) or a wide area network (WAN)), the Internet, and a telephone network.

Each of the first and second external electronic device 902 and 903 may be the same as or different from the blood glucose measurement apparatus 100. According to an embodiment of the present disclosure, the server 904, may include a group of one or more servers. All or some of operations executed by the blood glucose measurement apparatus 100 may be executed by one or more of the first external electronic device 902, the second external electronic device 903, and the server 904. When the blood glucose measurement apparatus 100 executes a certain function or service automatically or in response to a request, instead of or in addition to executing the certain function or service by the blood glucose measurement apparatus 100, the blood glucose measurement apparatus 100 may request another device (e.g., the first external electronic device 902, the second external electronic device 903, or the server 904) for at least a partial function related to the certain function or service. The device (e.g., the first external electronic device 902, the second external electronic device 903, or the server 904) may execute the requested function or an additional function, and may transmit the execution result to the blood glucose measurement apparatus 100. The blood glucose measurement apparatus 100 may provide the requested function or service as the received result or by processing the received result. To this end, for example, a cloud computing, distributed computing, or client-server computing technique may be used.

According to an embodiment of the present disclosure, the blood glucose measurement apparatus 100 may further include an input and output interface and a display.

The input and output interface may act as an interface capable of transmitting a command or data input from the user or another external device to other component(s) of the blood glucose measurement apparatus 100. In addition, the input and output interface may output a command or data received from other component(s) of the blood glucose measurement apparatus 100 to the user or another external device.

The display may include, for example, a liquid crystal display (LCD), a light-emitting diode (LED) display, an organic light-emitting diode (OLED) display, a microelectromechanical systems (MEMS) display, or an electronic paper display. The display may display various kinds of content (e.g., text, image, video, Icon, and symbol) to the user. The display may include a touchscreen, and in this case, the display may receive, for example, a touch, gesture, proximity, or hovering input using an electronic pen or a part of the body of the user.

The sensor 190 may include a microneedle for measuring glucose concentration, a motion detection sensor (e.g., an acceleration sensor, a geomagnetic sensor, and a gyro sensor), glasses equipped with a camera, an ECG sensor, a GSR sensor, a PPG sensor, a thermometer, a passometer, a motion sensor, and a GPS sensor.

Figure 14:
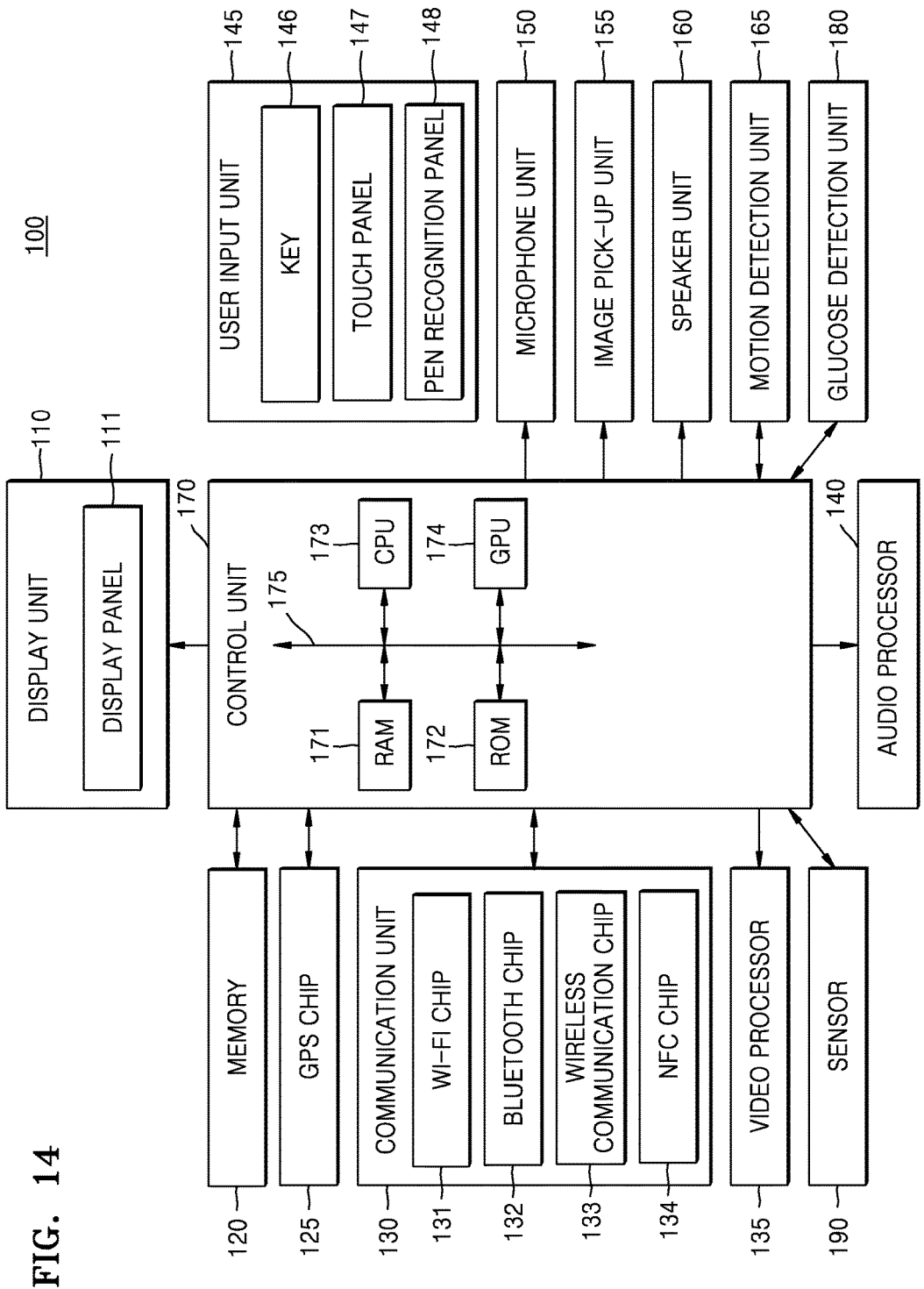
FIG. 14 is a block diagram illustrating a blood glucose measurement apparatus, according to another embodiment of the present disclosure.

FIG. 14 is a block diagram illustrating the blood glucose measurement apparatus 100, according to another embodiment of the present disclosure.

Referring to FIG. 14, the blood glucose measurement apparatus 100 may include at least one of a display unit 110, the memory 120, a GPS chip 125, the communication unit 130, a video processor 135, an audio processor 140, a user input unit 145, a microphone unit 150, an image pick-up unit 155, a speaker unit 160, a motion detection unit 165, the sensor 190, the control unit 170, and the glucose detection unit 180.

The sensor 190 may include a microneedle capable of measuring glucose concentration, a motion detection sensor (e.g., an acceleration sensor, a geomagnetic sensor, and a gyro sensor), glasses equipped with a camera, an ECG sensor, a GSR sensor, a PPG sensor, a thermometer, a passometer, a motion sensor, and a GPS sensor, but is not limited thereto.

The display unit 110 may include a display panel 111 and a controller for controlling the display panel 111. The display panel 111 may be implemented using various types of displays such as an LCD, an OLED display, an active-matrix OLED (AM-OLED) display, and a plasma display panel (PDP). The display panel 111 may be implemented to be flexible, transparent, or wearable. The display unit 110 may be coupled to a touch panel 147 of the user input unit 145 so as to configure a touch screen. For example, the touch screen may include an integrated module in which the display unit 110 and the touch panel 147 are coupled in a stacked structure.

The memory 120 may include at least one of an internal memory and an external memory.

The internal memory include at least one of volatile memories (e.g., dynamic random access memory (DRAM), static RAM (SRAM), and synchronous DRAM (SDRAM)), nonvolatile memories (e.g., one time programmable read-only memory (OTPROM), PROM, erasable and programmable ROM (EPROM), electrically EPROM (EEPROM), mask ROM, and flash ROM), a hard disk drive (HDD), and a solid state drive (SSD). According to an embodiment of the present disclosure, the control unit 170 may load a command or data received from at least one of the nonvolatile memories or other components on a volatile memory, and may process the loaded command or data. In addition, the control unit 170 may store data received from another component or generated data in a nonvolatile memory.

The external memory may include at least one of, for example, a compact flash (CF) memory, a secure digital (SD) memory, a micro-SD memory, a mini-SD memory, an extreme digital (xD) memory, and a memory stick.

The memory 120 may store various kinds of programs and data to be used for an operation of the blood glucose measurement apparatus 100. For example, the memory 120 may temporarily or semi-permanently store at least a portion of content to be displayed on a lock screen image.

The control unit 170 may control the display unit 110 to display a portion of the content stored in the memory 120 thereon. Specifically, the control unit 170 may display a portion of the content stored in the memory 120 on the display unit 110. In addition, when a user's gesture on one region of the display unit 110 is received, the control unit 170 may perform a control operation corresponding to the user's gesture.

The control unit 170 may include at least one of a RAM 171, a ROM 172, the CPU 173, the GPU 174, and the bus 175. The RAM 171, the ROM 172, the CPU 173, the GPU 174, and the like may be connected to each other via the bus 175.

The CPU 173 may access the memory 120 to boot the blood glucose measurement apparatus 100 by using the OS stored in the memory 120. In addition, the CPU 173 may perform various operations by using various kinds of programs, content, data and the like stored in the memory 120.

The ROM 172 stores a command set and the like for system booting. For example, when a turn-on command is input, to supply power to the blood glucose measurement apparatus 100, the CPU 173 may copy the OS stored in the memory 120 to the RAM 171 according to instructions stored in the ROM 172 and execute the OS to boot the system. If the booting is completed, the CPU 173 may copy various programs stored in the memory 120 to the RAM 171 and execute the copied programs to perform various operations. The GPU 174 may display a user interface (UI) image in a region of the display unit 110 if the blood glucose measurement apparatus 100 is completely booted. In detail, the GPU 174 may generate a screen image in which an electronic document including various objects such as content, icons, menus, and the like is displayed. The GPU 174 may compute attribute values such as a coordinate value, a shape, a size, a color, and the like of each of the objects to be displayed according to a layout of the screen. In addition, the GPU 174 may generate screen images having various layouts, which include objects, based on the computed attribute values. The screen images generated by the GPU 174 may be provided to the display unit 110 and displayed in respective regions of the display unit 110.

The GPS chip 125 may calculate a current location of the blood glucose measurement apparatus 100 by receiving GPS signals from GPS satellites. The control unit 170 may calculate a location of the user by using the GPS chip 125 when the user uses a navigation program or when a current location of the user is necessary.

The communication unit 130 may communicate with various types of external devices according to various types of communication schemes. The communication unit 130 may include at least one of a Wi-Fi chip 131, a Bluetooth chip 132, a wireless communication chip 133, and an NFC chip 134. The control unit 170 may communicate with various types of external devices by using the communication unit 130.

The Wi-Fi chip 131 and the Bluetooth chip 132 may perform communication in a Wi-Fi scheme and a Bluetooth scheme, respectively. When the Wi-Fi chip 131 or the Bluetooth chip 132 is used, various kinds of information may be transmitted and received by first transmitting and receiving various kinds of connection information, such as a service set identifier (SSID) and a session key, and then connecting communication using the connection information. The wireless communication chip 133 indicates a chip configured to perform communication according to various communication standards such as, for example, the Institute of Electrical and Electronics Engineers (IEEE), ZigBee, third generation (3G), and LTE. The NFC chip 134 indicates a chip operating in an NFC scheme using a 13.56 MHz band among various radio frequency identification (RF-ID) frequency bands such as 135 KHz, 13.56 MHz, 433 MHz, 860 to 960 MHz, and 2.45 GHz.

The video processor 135 may process video data included in content received via the communication unit 130 or stored in the memory 120. The video processor 135 may perform various kinds of image processing such as decoding, scaling, noise filtering, frame rate conversion, and size conversion on the video data.

The audio processor 140 may process audio data included in content received via the communication unit 130 or stored in the memory 120. The audio processor 140 may perform various kinds of processing such as decoding, amplification, and noise filtering on the audio data.

When a replay program for multimedia content is executed, the control unit 170 may operate the video processor 135 and the audio processor 140 to replay the multimedia content. The speaker unit 160 may output audio data generated by the audio processor 140.

The user input unit 145 may receive various instructions input by the user. The user input unit 145 may include at least one of a key 146, the touch panel 147, and a pen recognition panel 148.

The key 146 may include various types of keys, such as mechanical buttons and wheels, formed in various regions, such as a front part, a side part, and a rear part, of the exterior of a main body of the blood glucose measurement apparatus 100.

The touch panel 147 may detect a touch input of the user and output a touch event value corresponding to the detected touch signal. When the touch panel 147 is coupled to the display panel 111 to configure the touch screen, the touch screen may be implemented by various types of touch sensors, such as, for example, a capacitive overlay touch sensor, a resistive overlay touch sensor, and a piezoelectric touch sensor. The capacitive overlay touch sensor calculates touch coordinates by detecting micro electricity caused by the user's body when a portion of the user's body touches a surface of the touch screen. The resistive overlay touch sensor includes two electrode plates embedded in the touch screen and calculates by detecting a current flowing according to contact between the two electrode plates at a touched point. A touch event occurring on the touch screen may be generated by a finger of a human being, but the touch event may be generated by a conductive material capable of causing a change in a capacitance.

The pen recognition panel 148 may detect a proximity input or a touch input of a pen according to the use of a touch pen (e.g., a stylus pen or a digitizer pen) of the user and an output a pen proximity event or a pen touch event, according to the detected proximity input or touch input. The pen recognition panel 148 may be implemented in, for example, an electromagnetic resonance (EMR) scheme, and may detect a touch or proximity input according to a change in the intensity of an electromagnetic field due to proximity or a touch of the pen. In detail, the pen recognition panel 148 may include an electromagnetic induction coil sensor having a grid structure and an electronic signal processing unit configured to sequentially provide an alternating current (AC) signal having a certain frequency to each of loop coils of the electromagnetic induction coil sensor. If a pen having a built-in resonance circuit exists around the loop coils of the pen recognition panel 148, a magnetic field transmitted from a corresponding loop coil induces a current to the resonance circuit in the pen based on mutual electromagnetic induction. An induction magnetic field is generated based on the current by a coil forming the resonance circuit in the pen, and the pen recognition panel 148 may detect the induction magnetic field using a loop coil in a signal reception state, thereby detecting proximity or a touch position of the pen. The pen recognition panel 148 may be provided with a certain area such as, for example, an area by which a display area of the display panel 111 is covered, at a lower part of the display panel 111.

The microphone unit 150 may receive a voice of the user or other sounds and convert the received voice or sounds into audio data. The control unit 170 may use the user's voice, which is input through the microphone unit 150 in a call operation, or may convert the user's voice into audio data and store the audio data in the memory 120.

The image pick-up unit 155 may pick up a still image or a video under control of the user. The image pick-up unit 155 may be plural in number with a front camera, a rear camera, and the like.

When the image pick-up unit 155 and the microphone unit 150 are provided, the control unit 170 may perform a control operation according to a user's voice input through the microphone unit 150 or a user's motion recognized by the image pick-up unit 155. For example, the blood glucose measurement apparatus 100 may operate in a motion control mode or a voice control mode. When the blood glucose measurement apparatus 100 operates in the motion control mode, the control unit 170 may activate the image pick-up unit 155 to photograph the user, track a change in a user's motion, and perform a control operation corresponding to the change in the user's motion. When the blood glucose measurement apparatus 100 operates in the voice control mode, the control unit 170 may operate in a voice recognition mode by analyzing a user's voice input through the microphone unit 150 and performing a control operation according to the analyzed user's voice.

The motion detection unit 165 may detect a motion of the main body of the blood glucose measurement apparatus 100. The blood glucose measurement apparatus 100 may be rotated or leaned in various directions. In this case, the motion detection unit 165 may detect motion characteristics such as, for example, a rotation direction and an angle, and a gradient by using at least one of various sensors such as, for example, a geomagnetic sensor, a gyro sensor, and an acceleration sensor.

According to an embodiment of the present disclosure, the blood glucose measurement apparatus 100 may also include a USB port capable of connecting to a USB connector, various external input ports for connecting various external terminals, such as, for example, headset, mouse, and LAN terminals, a digital multimedia broadcasting (DMB) chip for receiving and processing a DMB signal, various sensors, and the like.

The names of the components of the blood glucose measurement apparatus 100, which have been described above, may vary. In addition, according to an embodiment of the present disclosure, the blood glucose measurement apparatus 100 may be configured to include at least one of the components described above, some components may be omitted, or additional components may be included.

One or more embodiments of the present disclosure may be implemented in a form of a recording medium including computer-executable instructions, such as a program module executed by a computer system. A non-transitory computer-readable medium may be an arbitrary available medium that may be accessed by a computer system, and may include all types of volatile and nonvolatile media and separated and non-separated media. In addition, the non-transitory computer-readable medium may include all types of computer storage media and communication media. The computer storage media may include all types of volatile and non-volatile and separated and non-separated media implemented by an arbitrary method or technique for storing information such as computer-readable instructions, a data structure, a program module, or other data. The communication media typically include computer-readable instructions, a data structure, a program module, other data of a modulated signal such as a carrier, other transmission mechanism, and arbitrary information delivery media.

While the disclosure has been shown and described with reference to certain embodiments thereof, it will be understood by those skilled in the art that various changes in form and detail may be made therein without departing from the spirit and scope of the disclosure as defined by the appended claims.

What is claimed is:
1. A blood glucose measurement apparatus comprising:
 a glucose detection unit configured to detect a glucose concentration in a body fluid of a user based on a glucose concentration measurement interval; and
 a wearable device configured to be worn by the user and wirelessly connected to the glucose detection unit, wherein the wearable device comprises:
  a control unit configured to:
   determine a first blood glucose level of the user based on a first glucose concentration detected by the glucose detection unit at a first measurement interval and transmitted to the wearable device by the glucose detection unit,
   change the glucose concentration measurement interval from the first measurement interval to a second measurement interval according to an occurrence of an event and information about the event, wherein the event comprises a determination of an action of the user and the information comprises predetermined information according to a performance and duration of the action, transmit the second measurement interval to the external glucose detection unit, and determine a second blood glucose level of the user based on a second glucose concentration detected by the glucose detection unit at the second measurement interval transmitted to the wearable device by the glucose detection unit.

2. The blood glucose measurement apparatus of claim 1, wherein the wearable device further comprises:

a communication unit configured to receive information about whether the event has occurred from a periphery device through short-range wireless communication.

3. The blood glucose measurement apparatus of claim 1, wherein the event comprises exercise performed by the user, and wherein the control unit changes the glucose concentration measurement interval from the first measurement interval to the second measurement interval based on the exercise performed by the user.

4. The blood glucose measurement apparatus of claim 3, wherein the control unit is further configured to determine an amount of exercise performed by the user from a movement sensor attached to the user, and wherein the control unit changes the glucose concentration measurement interval from the first measurement interval to the second measurement interval when the amount of exercise performed by the user exceeds a preset amount of exercise.

5. The blood glucose measurement apparatus of claim 1, wherein the event comprises food consumption by the user, and wherein the control unit changes the glucose concentration measurement interval from the first measurement interval to the second measurement interval based on the food consumption by the user.

6. The blood glucose measurement apparatus of claim 1, wherein the event comprises a determination that the user is in a sleeping state, and wherein the control unit changes the glucose concentration measurement interval from the first measurement interval to the second measurement interval based on the determination that the user is in the sleeping state.

7. The blood glucose measurement apparatus of claim 1, wherein the event comprises a determination that an amount of hormones of the user has changed, and wherein the control unit changes the glucose concentration measurement interval from the first measurement interval to the second measurement interval based on the determination that an amount of hormones of the user has changed.

8. The blood glucose measurement apparatus of claim 1, wherein the control unit changes the glucose concentration measurement interval from the first measurement interval to the second measurement interval by setting the second measurement interval as less than the first measurement interval according to an increase in a rate of change of the first blood glucose level of the user.

9. The blood glucose measurement apparatus of claim 1, wherein the control unit is further configured to determine whether a rate of change of the first blood glucose level of the user exceeds a threshold value, and wherein the control unit determines that the event has occurred when the rate of change of the first blood glucose level of the user exceeds the threshold value.

10. The blood glucose measurement apparatus of claim 1, wherein the control unit is further configured to determine a rate of change of the first glucose concentration over time, and wherein the control unit determines that the event has occurred according to a change in the rate of change of the first glucose concentration.

11. A blood glucose measurement method comprising:

detecting, by a blood glucose measurement apparatus, a first glucose concentration in a body fluid of a user based on a first measurement interval;

transmitting the first glucose concentration based on a first measurement interval to a wearable device;

determining, by the wearable device, a first blood glucose level of the user based on the first glucose concentration;

changing, by the wearable device, a glucose concentration measurement interval from the first measurement interval to a second measurement interval according to an occurrence of an event and information about the event, wherein the event comprises a determination of an action of the user and the information comprises predetermined information according to a performance and duration of the action;

transmitting the second measurement interval to the blood glucose measurement apparatus;

detecting, by the blood glucose measurement apparatus, a second glucose concentration in the body fluid based on the second measurement interval;

transmitting the second glucose concentration based on the second measurement interval to the wearable device; and determining, by the wearable device, a second blood glucose level of the user based on the second glucose concentration.

12. The blood glucose measurement method of claim 11, wherein information about whether the event has occurred is received from a periphery device through short-range wireless communication.

13. The blood glucose measurement method of claim 11, wherein the event comprises exercise performed by the user; and wherein the glucose concentration measurement interval is changed from the first measurement interval to the second measurement interval based on the exercise performed by the user.

14. The blood glucose measurement method of claim 13, further comprising:

determining an amount of exercise performed by the user from a movement sensor attached to the user, wherein the glucose concentration measurement interval is changed from the first measurement interval to the second measurement interval when the amount of exercise performed by the user exceeds a preset amount of exercise.

15. The blood glucose measurement method of claim 11, wherein the event comprises food consumption by the user; and wherein the glucose concentration measurement interval is changed from the first measurement interval to the second measurement interval based on the food consumption by the user.

16. The blood glucose measurement method of claim 11, wherein the event comprises a determination that the user is in a sleeping state; and wherein the glucose concentration measurement interval is changed from the first measurement interval to the second measurement interval based on the determination that the user is in the sleeping state.

17. The blood glucose measurement method of claim 11, wherein the event comprises a determination that an amount of hormones of the user has changed; and wherein the glucose concentration measurement interval is changed from the first measurement interval to the second measurement interval based on the determination that an amount of hormones of the user has changed.

18. The blood glucose measurement method of claim 11, further comprising:

determining whether a rate of change of the first blood glucose level of the user exceeds a threshold value;

determining that the event has occurred when the rate of change of the first blood glucose level exceeds the threshold value.

19. The blood glucose measurement method of claim 11, further comprising:

determining a rate of change of the first glucose concentration over time; and determining that the event has occurred according to a change in the determined rate of change of glucose concentration.

20. A non-transitory computer recording medium recorded with a computer-readable instruction, the instruction, which is executed by at least one processor, causing the processor to perform a method, the method comprising:

receiving, from a blood glucose detection unit, a first glucose concentration in a body fluid of a user based on a first measurement interval;

determining, by a wearable device, a first blood glucose level of the user based on the first glucose concentration;

changing, by the wearable device, a glucose concentration measurement interval from the first measurement interval to a second measurement interval according to an occurrence of an event and information about the event, wherein the event comprises a determination of an action of the user and the information comprises predetermined information according to a performance and duration of the action;

transmitting the second measurement interval to the blood glucose detection unit;

receiving a second glucose concentration from the blood glucose detection unit, the second glucose concentration being detected by the blood glucose detection unit in the body fluid based on the second measurement interval; and determining, by the wearable device, a second blood glucose level of the user based on the second glucose concentration.

* * * * *

UNITED STATES PATENT AND TRADEMARK OFFICE
CERTIFICATE OF CORRECTION

PATENT NO. : 10,165,968 B2
APPLICATION NO. : 15/148537
DATED : January 1, 2019
INVENTOR(S) : Hyoung-seon Choi et al.

Page 1 of 1

It is certified that error appears in the above-identified patent and that said Letters Patent is hereby corrected as shown below:

In the Claims

Column 31, Claim 19, Line 3, "determining a rate of change of the first glucose concen-" should read -- determining a rate of change of glucose concen- --

Signed and Sealed this
Ninth Day of July, 2019

Andrei Iancu
*Director of the United States Patent and Trademark Office*